US012697318B2

(12) United States Patent
Ogawa et al.

(10) Patent No.: US 12,697,318 B2
(45) **Date of Patent: *Aug. 4, 2026**

(54) ANTI-INFLAMMATORY AGENT CONTAINING RARE FATTY ACID

(71) Applicant: Noster Inc., Muko (JP)

(72) Inventors: Jun Ogawa, Kyoto (JP); Shigenobu Kishino, Kyoto (JP); Teruo Kawada, Kyoto (JP); Nobuyuki Takahashi, Kyoto (JP); Tsuyoshi Goto, Kyoto (JP); Tatsuya Sugawara, Kyoto (JP); Yasunori Yonejima, Muko (JP)

(73) Assignee: Noster Inc., Muko (JP)

( * ) Notice: Subject to any disclaimer, the term of this patent is extended or adjusted under 35 U.S.C. 154(b) by 189 days.

This patent is subject to a terminal disclaimer.

(21) Appl. No.: 16/953,129

(22) Filed: Nov. 19, 2020

(65) Prior Publication Data

US 2021/0069141 A1 Mar. 11, 2021

Related U.S. Application Data

(62) Division of application No. 15/113,714, filed as application No. PCT/JP2015/051844 on Jan. 23, 2015, now abandoned.

(30) Foreign Application Priority Data

Jan. 24, 2014 (JP) ................................ 2014-011866
Aug. 8, 2014 (JP) ................................ 2014-162982

(51) Int. Cl.

| | |
|---|---|
| ***A01N 43/00*** | (2006.01) |
| ***A01N 43/46*** | (2006.01) |
| ***A23L 33/12*** | (2016.01) |
| ***A61K 31/20*** | (2006.01) |
| ***A61K 31/201*** | (2006.01) |
| ***A61K 31/202*** | (2006.01) |
| ***A61K 31/55*** | (2006.01) |
| ***A61K 45/06*** | (2006.01) |

(52) U.S. Cl.
CPC .............. *A61K 31/20* (2013.01); *A23L 33/12* (2016.08); *A61K 31/201* (2013.01); *A61K 31/202* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 4,908,384 A * | 3/1990 | Ho | C07C 59/42 | 554/219 |
| 5,260,336 A * | 11/1993 | Forse | A61K 31/20 | 514/549 |
| 9,707,200 B2 | 7/2017 | Ogawa et al. | | |
| 2005/0214241 A1* | 9/2005 | Kandil | A61Q 19/00 | 424/74 |
| 2010/0035989 A1 | 2/2010 | Schwartz et al. | | |
| 2011/0190389 A1* | 8/2011 | Arterburn | A61P 39/06 | 514/475 |
| 2012/0142773 A1 | 6/2012 | Kelliher et al. | | |
| 2013/0274327 A1 | 10/2013 | Arita et al. | | |
| 2015/0125911 A1 | 5/2015 | Ogawa et al. | | |
| 2015/0342916 A1 | 12/2015 | Ogawa et al. | | |
| 2016/0000739 A1 | 1/2016 | Ogawa et al. | | |
| 2017/0000752 A1 | 1/2017 | Ogawa et al. | | |

FOREIGN PATENT DOCUMENTS

| | | | | |
|---|---|---|---|---|
| CN | 101611894 A | * 12/2009 | | |
| CN | 102458391 A | 5/2012 | | |
| JP | 3103274 B2 | * 10/2000 | | |
| JP | 2003073329 A | * 3/2003 | | |
| JP | 2005-008594 A | 1/2005 | | |
| JP | 2009-051732 A | 3/2009 | | |
| JP | 2009-545527 A | 12/2009 | | |
| JP | 2011-184411 A | 9/2011 | | |
| KR | 10-0793081 B1 | * 1/2008 | | |
| KR | 101281470 B1 | * 7/2013 | | |
| WO | WO-9310776 A1 | * 6/1993 | A61K 31/20 | |
| WO | WO-9600584 A1 | * 1/1996 | A61K 2300/00 | |
| WO | WO 1999/016435 A1 | 4/1999 | | |
| WO | WO-2004002234 A1 | * 1/2004 | A23D 9/007 | |
| WO | WO-2004084829 A2 | * 10/2004 | A61K 31/20 | |
| WO | WO-2007069758 A1 | * 6/2007 | A61K 31/19 | |
| WO | WO 2012/023254 A1 | 2/2012 | | |
| WO | WO-2013003689 A2 | * 1/2013 | A23D 9/007 | |
| WO | WO 2013/168310 A1 | 11/2013 | | |
| WO | WO 2014/069227 A1 | 5/2014 | | |
| WO | WO 2014/129384 A1 | 8/2014 | | |

OTHER PUBLICATIONS

Haviv et al. (Structural requirements for the inhibition of 5-lipoxygenase by 15-hydroxyeicosa-5,8, 11,13-tetraenoic acid analogs. Journal of Medicinal Chemistry vol. 30 Issue: 2 pp. 254-263 Journal; Comparative Study; Article 1987) (Year: 1987).*
Herrmann et al. ("Impaired phagocytosis of apoptotic cell material by monocyte-derived macrophages from patients with systemic lupus erythematosus." Arthritis & Rheumatism 41.7 (1998): 1241-1250.*
Peng et al. (Regulatory Mechanism of M1/M2 Macrophage Polarization in the Development of Autoimmune Diseases. Mediators Inflamm. Jun. 8, 2023;2023:8821610. doi: 10.1155/2023/8821610. PMID: 37332618; PMCID: PMC10270764.*
Boddu et al., "Anti-inflammatory effects of a novel ricinoleic acid poloxamer gel system for transdermal delivery," *Int. J. Pharm.*, 479(1): 207-211 (2015).
Cipollina et al., "Cyclooxygenase-2 Generates Anti-inflammatory Omega-3 fatty acid Derivatives in Activated Macrophages," *Free Radical Biology and Medicine*, 47(Suppl. 1): S212, abstract 313 (2009).

(Continued)

*Primary Examiner* — Layla Soroush
(74) *Attorney, Agent, or Firm* — Leydig, Voit & Mayer, Ltd.

(57) ABSTRACT

The present invention provides an anti-inflammatory agent containing a rare fatty acid such as hydroxylated fatty acid, oxo fatty acid and the like, and further, food, pharmaceutical product and the like containing the anti-inflammatory agent.

3 Claims, 11 Drawing Sheets

Specification includes a Sequence Listing.

(56) References Cited

OTHER PUBLICATIONS

Haas et al., "Simplifying biodiesel production: The direct or in situ transesterification of algal biomass," *Eur. J. Lipid Sci. Technol.*, 113(10): 1219-1229 (2011).
Kim et al., "9-oxo-10(E), 12(E)-octadecadienoic acid derived from tomato is a potent PPARα agonist to decrease triglyceride accumulation in mouse primary hepatocytes," *Mol. Nutr. Food. Res.*, 55(4): 585-593 (2011).
Kim et al., "Potent PPARα Activator Derived from Tomato Juice, 13-oxo-9,11-Octadecadienoic Acid, Decreases Plasma and Hepatic Triglyceride in Obese Diabetic Mice," *PLoS One*, 7(2): e31317 (2012).
Kishino et al., "Polyunsaturated fatty acid saturation by gut lactic acid bacteria affecting host lipid composition," *Proc. Natl. Acad. Sci. U.S.A.*, 110(44): 17808-17813 (2013).
Murakami et al., "New class of linoleic acid metabolites biosynthesized by corn and rice lipoxygenases: Suppression of proinflammatory mediator expression via attenuation of MAPK- and Akt-, but not PPARγ-, dependent pathways in stimulated macrophages," *Biochem. Pharmacol.*, 70(1): 1330-1342 (2005).
Tanabe et al., "Production of unique hydroxy fatty acid using lactic acid bacteria," *Abstracts of the Annual Conference of the Japan Society for Bioscience, Biotechnology, and Agrochemistry*, 2007: 45, abstract 2A11p13 (2007).
Tunaru et al., "Castor oil induces laxation and uterus contraction via ricinoleic acid activating prostaglandin $EP_3$ receptors," *PNAS*, 109(23): 9179-9184 (2012).
Vieira et al., "Effect of ricinoleic acid in acute and subchronic experimental models of inflammation," *Mediators Inflamm.*, 9(5): 223-228 (2000).
China National Intellectual Property Administration, Search Report in Chinese Patent Application No. 20158005505.X (Feb. 15, 2019).
Japanese Patent Office, International Search Report in International Patent Application No. PCT/JP2015/051844 (Apr. 28, 2015).
U.S. Appl. No. 15/113,714, filed Jul. 22, 2016.
Grechkin et al., "The lipoxygenase pathway in tulip (*Tulipa gesneriana*): detection of the ketol route," *Biochem. J.*, 352(Pt. 2): 501-509 (2000).
Nakajima et al., "Synthesis of 13-Oxo-(Z)-9-octadecenoic Acid and 15-Oxo-(Z)-11-icosenoic Acid, Arrestants of *Oryzaephilus surinamensis* L.," *Biosci. Biotech. Biochem.*, 61(3): 551-552 (1997).
Shiraki et al., "α,β-Unsaturated Ketone Is a Core Moiety of Natural Ligands for Covalent Binding to Peroxisome Proliferator-activated Receptor γ," *J. Biol. Chem.*, 280(14): 14145-14153 (2005).
Belarbi et al., "TNF-α Protein Synthesis Inhibitor Restores Neuronal Function and Reverses Cognitive Deficits Induced by Chronic Neuroinflammation," *J. Neuroinflammation.*, 9: 23 (2012).
De Meyer et al., "Therapeutic Strategies to Deplete Macrophages in Atherosclerotic Plaques," *Br. J. Clin. Pharmacol.*, 74(2): 246-263 (2012).
Galanos et al., "Mechanisms of Endotoxin Shock and Endotoxin Hypersensitivity," *Immunobiol.*, 187: 346-356 (1993).
Han et al., "Influence of Mild Hypothermia on Inducible Nitric Oxide Synthase Expression and Reactive Nitrogen Production in Experimental Stroke and Inflammation," *J. Neurosci.*, 22(10): 3921-3928 (2002).
Kasraie et al., "Role of Macrophages in the Pathogenesis of Atopic Dermatitis," *Mediators Inflamm.*, 2013: 942375 (2013).
Kinne et al., "Macrophages in Rheumatoid Arthritis," *Arthritis Res.*, 2(3): 189-202 (2000).
Li et al., "Microglia-Derived Macrophages in Early Multiple Sclerosis Plaques," *Neuropathol. Appl. Neurobiol.*, 22(3): 207-215 (1996).
Martin et al., "Resident Macrophages Initiating and Driving Inflammation in a Monosodium Urate Monohydrate Crystal-Induced Murine Peritoneal Model of Acute Gout," *Arthritis Rheum.*, 60(1): 281-289 (2009).
Nikolic-Paterson et al., "The Role of Macrophages in Glomerulonephritis," *Nephrol. Dial. Transplant.*, 16 [Suppl 5]: 3-7 (2001).
Sugimoto et al., "Non-targeted Metabolite Profiling in Activated Macrophage Secretion," *Metabolomics*, 8: 624-633 (2012).
Watanabe et al., "Hepatocellular Oxidative DNA Injury Induced by Macrophage-Derived Nitric Oxide," *Free Radic. Biol. Med.*, 30(9): 1019-1028 (2001).
Arora et al., "The ATP-Binding Cassette Gene ABCF1 Functions as an E2 Ubiquitin-Conjugating Enzyme Controlling Macrophage Polarization to Dampen Lethal Septic Shock," *Immunity*, 50: 418-431 (2019).
Lin et al., "Stefin B alleviates the gouty arthritis in mice by inducing the M2 polarization of macrophages," *Naunyn-Schmiedeberg's Archives of Pharmacology*, 397: 5677-5688 (2024).
Weng et al., "Phenotypic Screening-Based Identification of 3,4-Disubstituted Piperidine Derivatives as Macrophage M2 Polarization Modulators: An Opportunity for Treating Multiple Sclerosis," *J. Med. Chem.*, 62: 3268-3285 (2019).
Wu et al., "Akt2 Affects Periodontal Inflammation via Altering the M1/M2 Ratio," *J. Dent. Res.*, 99(5): 577-587 (2020).
Yao et al., "Microglial polarization: novel therapeutic mechanism against Alzheimer's disease," *Inflammopharmacology*, 28(1): 95-110 (2020).
Zheng et al., "Exosomes from LPS-stimulated macrophages induce neuroprotection and functional improvement after ischemic stroke by modulating microglial polarization," *Biomater. Sci.*, 7: 2037-2049 (2019).

* cited by examiner

| | |
|---|---|
| * basal medium | : PRMI1640, 10% FBS, 1% Penicillin/Streptomycin, 55μM β-mercaptoethanol<br>20%(v/v) L929 conditioned medium |

ANTI-INFLAMMATORY AGENT CONTAINING RARE FATTY ACID

CROSS-REFERENCE TO RELATED APPLICATIONS

This patent application is a divisional of copending U.S. patent application Ser. No. 15/113,714, filed on Jul. 22, 2016, which is the U.S. national phase of International Patent Application No. PCT/JP2015/051844, filed on Jan. 23, 2015, which claims the benefit of Japanese Patent Application No. 2014-011866, filed Jan. 24, 2014, and Japanese Patent Application No. 2014-162982, filed Aug. 8, 2014, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 14,121 bytes ASCII (Text) file named "751327Sequence-Listing.txt," created Nov. 18, 2020.

TECHNICAL FIELD

The present invention relates to an anti-inflammatory agent containing a rare fatty acid. More particularly, the present invention relates to an anti-inflammatory agent utilizing the physiological function, for example, an action to suppress an inflammation reaction in vivo, of rare fatty acids such as oxo fatty acid, hydroxy fatty acid and the like. The present invention also relates to a food, a pharmaceutical product, a feed and the like containing the agent.

BACKGROUND ART

Inflammation is a defense reaction of living organisms which is observed when biological tissues are injured by bacterial infection, action of physicochemical factor and the like, wherein the causal substance of injury and injured tissues are removed thereby. As regards inflammatory reaction in living organisms, it is known that nitric oxide (NO) produced by M1 macrophage acts as a mediator. While NO acts as a biological defense factor, it exacerbates inflammation when produced in large amounts during inflammation. For example, in adipose tissue in obese state, inflammation is promoted by mutual activation of activated M1 macrophage and adipocyte and a disease state is induced. Therefore, an anti-inflammatory action of a substance that suppresses NO production by M1 macrophage is expected.

As a fatty acid derivative showing an anti-inflammatory action, hydroxylated fatty acids produced by lipoxygenase have been reported. For example, when a plant-derived lipoxygenase is used, 9-hydroxy-trans-10,cis-12-octadecadienoic acid, 13-hydroxy-cis-9,trans-11-octadecadienoic acid are produced from linoleic acid; 13-hydroxy-10-oxo-trans-11-octadecenoic acid, 9-hydroxy-13-oxo-trans-10-octadecenoic acid, 9-hydroxy-10-oxo-cis-12-octadecenoic acid, 13-hydroxy-12-oxo-cis-9-octadecenoic acid are further produced by a combined use with hydroxy peroxide isomerase, and these hydroxylated fatty acids and oxo fatty acids are reported to have an anti-inflammatory action (patent document 1). Also, as endogenous anti-inflammatory lipid mediator in mammals, epoxy form and hydroxylated form of ω3 fatty acids such as eicosapentaenoic acid (EPA), docosahexaenoic acid (DHA) and the like, which are produced by the action of oxidizing enzymes such as lipoxygenase, monooxygenase and the like, have been reported (patent document 2).

As for rare fatty acids such as hydroxylated fatty acid, oxo fatty acid and the like, since a part of oxo fatty acids such as 9-oxo-octadecadienoic acid, 13-oxo-octadecadienoic acid and the like contained in tomato have been reported to have an activity to improve lifestyle-related diseases, such as lipid metabolism improvement and the like (patent document 3, non-patent documents 1, 2), the physiological functions of rare fatty acids are drawing attention.

As regards production of rare fatty acids such as oxo fatty acid, hydroxylated fatty acid and the like, a production method of C10-position hydroxylated fatty acid and C10-position oxo fatty acid, each having 18 carbon atoms, which uses hydration dehydrase derived from *Lactobacillus plantarum*, and which was found by the inventors, has been reported (patent document 4). In addition, a metabolism improving effect (patent document 5), and an intestine protective action (patent document 6) relating to these C10-position hydroxylated fatty acid and C10-position oxo fatty acid have also been reported. However, the physiological functions other than metabolism improvement and intestinal protection, for example, physiological functions such as anti-inflammatory action and the like, of these hydroxylated fatty acid, oxo fatty acid, as well as hydroxylated fatty acid and oxo fatty acid, each having a carbon atom number other than 18 or hydroxylated fatty acid and oxo fatty acid, each having hydroxyl group, carbonyl group at a position other than C10-position are unknown.

DOCUMENT LIST

Patent Documents patent document 1: JP-A-2005-008594
patent document 2: WO 2012/023254
patent document 3: JP-A-2011-184411
patent document 4: WO 2013/168310
patent document 5: WO 2014/069227
patent document 6: WO 2014/129384

Non-Patent Document non-patent document 1: Kim Y-I, (2011), Mol. Nutr. Food Res., vol. 55, p. 585-593
non-patent document 2: Kim Y-I, (2012), PLoS ONE, vol. 7, no. 2, e31317

SUMMARY OF THE INVENTION

Problems to be Solved by the Invention

An object of the present invention is to provide a novel anti-inflammatory agent containing a rare fatty acid, which suppresses an inflammatory reaction.

Means of Solving the Problems

The present inventors have conducted intensive studies in view of the above-mentioned problems and found that rare fatty acids such as a C10-position hydroxylated fatty acid having 18 carbon atoms and a C10-position oxo fatty acid having 18 carbon atoms, obtained using a fatty acid saturating enzyme group derived from *Lactobacillus plantarum* and a chemical oxidation reaction, and a C13-position hydroxylated fatty acid having 18 carbon atoms and a C13-position oxo fatty acid having 18 carbon atoms, obtained using a hydration enzyme derived from *Lactobacillus acidophilus* and a chemical oxidation reaction and the like, which were found by the inventors, have a conventionally-unknown anti-inflammatory action based on an action to suppress NO production by M1 macrophage. In addition, the present inventors have found that the above-mentioned rare fatty acids have an effect to increase resistance of cells to $H_2O_2$ stress, and an effect to increase expression of an anti-oxidant enzyme HO-1 mRNA. Furthermore, the present inventors have found that the above-mentioned rare fatty acids suppress differentiation of monocyte and macrophage into M1 macrophage by directly or indirectly inducing differentiation of monocyte and macrophage into M2 macrophage.

The present invention has been completed based on the above findings.

Accordingly, the present invention provides the following:

[1] An anti-inflammatory agent comprising the following fatty acid:

(1) a fatty acid having 18 carbon atoms and a hydroxyl group or carbonyl group at the 10-position, (2) a fatty acid having 18 carbon atoms and a hydroxyl group or carbonyl group at the 13-position, (3) a fatty acid having 18 or 20 carbon atoms and a hydroxyl group or carbonyl group at the 12-position, (4) a fatty acid having 20 carbon atoms and a hydroxyl group or carbonyl group at the 15-position, or (5) a fatty acid having 16 carbon atoms and a hydroxyl group or carbonyl group at the 10-position;

[2] the agent of [1], comprising the following fatty acid:

(1) a saturated fatty acid or an unsaturated fatty acid having a trans double bond at the 11-position or at least one cis double bond at the 6-position, the 12-position, the 15-position, which has 18 carbon atoms and a hydroxyl group or carbonyl group at the 10-position, (2) a saturated fatty acid or an unsaturated fatty acid having at least one cis double bond at the 6-position, the 9-position, the 15-position, which has 18 carbon atoms and a hydroxyl group or carbonyl group at the 13-position, (3) a saturated fatty acid or an unsaturated fatty acid having at least one cis double bond at the 5-position, the 8-position, the 9-position, the 14-position, the 17-position, which has 18 or 20 carbon atoms and a hydroxyl group or carbonyl group at the 12-position, (4) an unsaturated fatty acid having at least one cis double bond at the 5-position, the 8-position, the 11-position, the 17-position, which has 20 carbon atoms and a hydroxyl group or carbonyl group at the 15-position, or (5) a saturated fatty acid having 16 carbon atoms and a hydroxyl group or carbonyl group at the 10-position;

[3] the agent of [2], comprising the following fatty acid:

(1) a saturated fatty acid or an unsaturated fatty acid having a trans double bond at the 11-position or at least one cis double bond at the 6-position, the 12-position, which has 18 carbon atoms and a hydroxyl group or carbonyl group at the 10-position, (2) a saturated fatty acid or an unsaturated fatty acid having at least one cis double bond at the 6-position, the 9-position, the 15-position, which has 18 carbon atoms and a hydroxyl group is or carbonyl group at the 13-position, or (3) saturated fatty acid having 18 carbon atoms and a hydroxyl group at the 12-position;

[4] the agent of [2], wherein (1) the saturated fatty acid or the unsaturated fatty acid having a trans double bond at the 11-position or at least one cis double bond at the 6-position, the 12-position, the 15-position, which has 18 carbon atoms and a hydroxyl group or carbonyl group at the 10-position, is 10-hydroxy-cis-12-octadecenoic acid, 10-hydroxy-cis-12,cis-15-octadecadienoic acid, 10-hydroxy-cis-6,cis-12-octadecadienoic acid, 10-hydroxy-cis-6,cis-12,cis-15-octadecatrienoic acid, 10,12-dihydroxy-octadecanoic acid, 10-hydroxy-octadecanoic acid, 10-hydroxy-cis-15-octadecenoic acid, 10-hydroxy-cis-6-octadecenoic acid, 10-hydroxy-cis-6,cis-15-octadecadienoic acid, 10-hydroxy-trans-11-octadecenoic acid, 10-hydroxy-trans-11,cis-15-octadecadienoic acid, 10-hydroxy-cis-6,trans-11-octadecadienoic acid, 10-hydroxy-cis-6,trans-11,cis-15-octadecatrienoic acid, 10-oxo-cis-12-octadecenoic acid, 10-oxo-cis-12,cis-15-octadecadienoic acid, 10-oxo-cis-6,cis-12-octadecadienoic acid, 10-oxo-cis-6,cis-12,cis-15-octadecatrienoic acid, 10-oxo-octadecanoic acid, 10-oxo-cis-6-octadecenoic acid, 10-oxo-cis-15-octadecenoic acid, 10-oxo-cis-6,cis-15-octadecadienoic acid, 10-oxo-trans-11-octadecenoic acid, 10-oxo-cis-6, trans-11-octadecadienoic acid, 10-oxo-trans-11,cis-15-octadecadienoic acid or 10-oxo-cis-6,trans-11,cis-15-octadecatrienoic acid, (2) the saturated fatty acid or the unsaturated fatty acid having at least one cis double bond at the 6-position, the 9-position, the 15-position, which has 18 carbon atoms and a hydroxyl group or carbonyl group at the 13-position, is 13-hydroxy-cis-9-octadecenoic acid, 13-hydroxy-cis-6,cis-9-octadecadienoic acid, 13-hydroxy-cis-9,cis-15-octadecadienoic acid, 13-hydroxy-cis-6,cis-9,cis-15-octadecatrienoic acid, 10,13-dihydroxy-octadecanoic acid, 10,13-dihydroxy-cis-6-octadecenoic acid, 10,13-dihydroxy-cis-15-octadecenoic acid, 10,13-dihydroxy-cis-6,cis-15-octadecadienoic acid, 10-oxo-13-hydroxy-octadecanoic acid, 10-oxo-13-hydroxy-cis-6-octadecenoic acid, 10-oxo-13-hydroxy-cis-15-octadecenoic acid, 10-oxo-13-hydroxy-cis-6,cis-15-octadecadienoic acid, 13-hydroxy-cis-5,cis-9-octadecadienoic acid, 13-hydroxy-trans-5,cis-9-octadecadienoic acid, 13-oxo-cis-9-octadecenoic acid, 13-oxo-cis-6,cis-9-octadecadienoic acid, 13-oxo-cis-9,cis-15-octadecadienoic acid, 13-oxo-cis-6,cis-9,cis-15-octadecatrienoic acid, 10,13-dioxo-octadecanoic acid, 10,13-dioxo-cis-6-octadecenoic acid, 10,13-dioxo-cis-15-octadecenoic acid, 10,13-dioxo-cis-6,cis-15-octadecadienoic acid, 13-oxo-cis-5,cis-9-octadecadienoic acid or 13-oxo-trans-5,cis-9-octadecadienoic acid, (3) the saturated fatty acid or the unsaturated fatty acid having at least one cis double bond at the 5-position, the 8-position, the 9-position, the 14-position, the 17-position, which has 18 or 20 carbon atoms and a hydroxyl group or carbonyl group at the 12-position, is 12-hydroxy-octadecanoic acid, 12-hydroxy-cis-14-eicosenoic acid, 12-hydroxy-cis-14,cis-17-eicosadienoic acid, 12-hydroxy-cis-8,cis-14-eicosadienoic acid, 12-hydroxy-cis-5,cis-8-eicosadienoic acid, 12-hydroxy-cis-8,cis-14,cis-17-eicosatrienoic acid, 12-hydroxy-cis-5,cis-8,cis-14-eicosatrienoic acid, 12-oxo-octadecanoic acid, 12-oxo-cis-9-octadecenoic acid, 12-oxo-cis-14-eicosenoic acid, 12-oxo-cis-14,cis-17-eicosadienoic acid, 12-oxo-cis-8,cis-14-eicosadienoic acid, 12-oxo-cis-5,cis-8-eicosadienoic acid, 12-oxocis-8,cis-14,cis-17-eicosatrienoic acid, or 12-oxo-cis-5, cis-8,cis-14-eicosatrienoic acid, (4) the unsaturated fatty acid having at least one cis double bond at the 5-position, the 8-position, the 11-position, the 17-position, which has 20 carbon atoms and a hydroxyl group or carbonyl group at the 15-position, is 15-hydroxy-cis-11-eicosenoic acid, 15-hydroxy-cis-11,cis-17-eicosadienoic acid, 15-hydroxy-cis-8,cis-11-eicosadienoic acid, 15-hydroxy-cis-5,cis-8,cis-11-eicosatrienoic acid, 15-hydroxy-cis-8,cis-11,cis-17-eicosatrienoic acid, 15-hydroxy-cis-5,cis-11-eicosadienoic acid, 15-hydroxy-cis-5,cis-11,cis-17-eicosatrienoic acid, 15-oxo-cis-11-eicosenoic acid, 15-oxo-cis-11,cis-17-eicosadienoic acid, 15-oxo-cis-8, cis-11-eicosadienoic acid, 15-oxo-cis-5,cis-8,cis-11-eicosatrienoic acid, 15-oxo-cis-8,cis-11,cis-17-eicosatrienoic acid, 15-oxo-cis-5,cis-11-eicosadienoic acid or 15-oxo-cis-5,cis-11,cis-17-eicosatrienoic acid, (5) the saturated fatty acid having 16 carbon atoms and a hydroxyl group or carbonyl group at the 10-position is 10-hydroxy-hexadecanoic acid or 10-oxo-hexadecanoic acid;

[5] the agent of [3], wherein (1) the saturated fatty acid or the unsaturated fatty acid having a trans double bond at the 11-position or at least one cis double bond at the 6-position, the 12-position, which has 18 carbon atoms and a hydroxyl group or carbonyl group at the 10-position, is 10-hydroxy-cis-12-octadecenoic acid, 10-hydroxy-octadecanoic acid, 10-oxo-cis-12-octadecenoic acid, 10-hydroxy-cis-12, cis-15-octadecadienoic acid, 10-hydroxy-cis-6,cis-12-octadecadienoic acid, 10-oxo-cis-12,cis-15-octadecadienoic acid, 10-oxo-cis-6,cis-12-octadecadienoic acid, 10-oxo-trans-11-octadecenoic acid, 10-oxo-trans-11, cis-15-octadecadienoic acid or 10-oxo-cis-6,trans-11-octadecadienoic acid, (2) the saturated fatty acid or the unsaturated fatty acid having at least one cis double bond at the 6-position, the 9-position, the 15-position, which has 18 carbon atoms and a hydroxyl group or carbonyl group at the 13-position, is 13-hydroxy-cis-9-octadecenoic acid, 13-hydroxy-cis-6,cis-9-octadecadienoic acid, 13-hydroxy-cis-9,cis-15-octadecadienoic acid, 10,13-dihydroxy-octadecanoic acid, 10,13-dihydroxy-cis-6-octadecenoic acid, 10,13-dihydroxy-cis-15-octadecenoic acid, 13-oxo-cis-9-octadecenoic acid, 13-oxo-cis-6,cis-9-octadecadienoic acid, or 13-oxo-cis-9,cis-15-octadecadienoic acid, or (3) the saturated fatty acid having 18 carbon atoms and a hydroxyl group at the 12-position is 12-hydroxy-octadecanoic acid;

[6] the agent of any one of [1]-[5] for use for the prophylaxis or improvement of an inflammatory disease involving macrophage;

[7] the agent of any one of [1]-[5], which is a food or a food additive;

[8] the agent of any one of [1]-[5], which is a pharmaceutical product;

[9] the agent of any one of [1]-[5], which is a feed or a feed additive;

[10] an M1 macrophage inhibitor comprising the following fatty acid:

(1) a fatty acid having 18 carbon atoms and a hydroxyl group or carbonyl group at the 10-position, (2) a fatty acid having 18 carbon atoms and a hydroxyl group or carbonyl group at the 13-position, (3) a fatty acid having 18 or 20 carbon atoms and a hydroxyl group or carbonyl group at the 12-position, (4) a fatty acid having 20 carbon atoms and a hydroxyl group or carbonyl group at the 15-position, or (5) a fatty acid having 16 carbon atoms and a hydroxyl group or carbonyl group at the 10-position;

[11] the inhibitor of [10], comprising the following fatty acid:

(1) a saturated fatty acid or an unsaturated fatty acid having a trans double bond at the 11-position or at least one cis double bond at the 6-position, the 12-position, the 15-position, which has 18 carbon atoms and a hydroxyl group or carbonyl group at the 10-position, (2) a saturated fatty acid or an unsaturated fatty acid having at least one cis double bond at the 6-position, the 9-position, the 15-position, which has 18 carbon atoms and a hydroxyl group or carbonyl group at the 13-position, (3) a saturated fatty acid or an unsaturated fatty acid having at least one cis double bond at the 5-position, the 8-position, the 9-position, the 14-position, the 17-position, which has 18 or 20 carbon atoms and a hydroxyl group or carbonyl group at the 12-position, (4) an unsaturated fatty acid having at least one cis double bond at the 5-position, the 8-position, the 11-position, the 17-position, which has 20 carbon atoms and a hydroxyl group or carbonyl group at the 15-position, or, (5) a saturated fatty acid having 16 carbon atoms and a hydroxyl group or carbonyl group at the 10-position;

[12] the inhibitor of [11], comprising the following fatty acid:

(1) a saturated fatty acid or an unsaturated fatty acid having a trans double bond at the 11-position or at least one cis double bond at the 6-position, the 12-position, which has 18 carbon atoms and a hydroxyl group or carbonyl group at the 10-position, (2) a saturated fatty acid or an unsaturated fatty acid having at least one cis double bond at the 6-position, the 9-position, the 15-position, which has 18 carbon atoms and a hydroxyl group or carbonyl group at the 13-position, or (3) a saturated fatty acid having 18 carbon atoms and a hydroxyl group at the 12-position;

[13] the inhibitor of [11], wherein (1) the saturated fatty acid or the unsaturated fatty acid having a trans double bond at the 11-position or at least one cis double bond at the 6-position, the 12-position, the 15-position, which has 18 carbon atoms and a hydroxyl group or carbonyl group at the 10-position, is 10-hydroxy-cis-12-octadecenoic acid, 10-hydroxy-cis-12,cis-15-octadecadienoic acid, 10-hydroxy-cis-6,cis-12-octadecadienoic acid, 10-hydroxy-cis-6,cis-12,cis-15-octadecatrienoic acid, 10,12-dihydroxy-octadecanoic acid, 10-hydroxy-octadecanoic acid, 10-hydroxy-cis-15-octadecenoic acid, 10-hydroxy-cis-6-octadecenoic acid, 10-hydroxy-cis-6,cis-15-octadecadienoic acid, 10-hydroxy-trans-11-octadecenoic acid, 10-hydroxy-trans-11,cis-15-octadecadienoic acid, 10-hydroxy-cis-6,trans-11-octadecadienoic acid, 10-hydroxy-cis-6,trans-11,cis-15-octadecatrienoic acid, 10-oxo-cis-12-octadecenoic acid, 10-oxo-cis-12, cis-15-octadecadienoic acid, 10-oxo-cis-6,cis-12-octadecadienoic acid, 10-oxo-cis-6,cis-12,cis-15-octadecatrienoic acid, 10-oxo-octadecanoic acid, 10-oxo-cis-6-octadecenoic acid, 10-oxo-cis-15-octadecenoic acid, 10-oxo-cis-6,cis-15-octadecadienoic acid, 10-oxo-trans-11-octadecenoic acid, 10-oxo-cis-6, trans-11-octadecadienoic acid, 10-oxo-trans-11,cis-15-octadecadienoic acid or 10-oxo-cis-6,trans-11,cis-15-octadecatrienoic acid, (2) the saturated fatty acid or the unsaturated fatty acid having at least one cis double bond at the 6-position, the 9-position, the 15-position, which has 18 carbon atoms and a hydroxyl group or carbonyl group at the 13-position, is 13-hydroxy-cis-9-octadecenoic acid, 13-hydroxy-cis-6,cis-9-octadecadienoic acid, 13-hydroxy-cis-9,cis-15-octadecadienoic acid, 13-hydroxy-cis-6,cis-9,cis-15-octadecatrienoic acid, 10,13-dihydroxy-octadecanoic acid, 10,13-dihydroxy-cis-6-octadecenoic acid, 10,13-dihydroxy-cis-15-octadecenoic acid, 10,13-dihydroxy-cis-6,cis-15-octadecadienoic acid, 10-oxo-13-hydroxy-octadecanoic acid, 10-oxo-13-hydroxy-cis-6-octadecenoic acid, 10-oxo-13-hydroxy-cis-15-octadecenoic acid, 10-oxo-13-hydroxy-cis-6,cis-15-octadecadienoic acid, 13-hydroxy-cis-5,cis-9-octadecadienoic acid, 13-hydroxy-trans-5,cis-9-octadecadienoic acid, 13-oxo-cis-9-octadecenoic acid, 13-oxo-cis-6,cis-9-octadecadienoic acid, 13-oxo-cis-9,cis-15-octadecadienoic acid, 13-oxo-cis-6,cis-9,cis-15-octadecatrienoic acid, 10,13-dioxo-octadecanoic acid, 10,13-dioxo-cis-6-octadecenoic acid, 10,13-dioxo-cis-15-octadecenoic acid, 10,13-dioxo-cis-6,cis-15-octadecadienoic acid, 13-oxo-cis-5,cis-9-octadecadienoic acid or 13-oxo-trans-5,cis-9-octadecadienoic acid, (3) the saturated fatty acid or the unsaturated fatty acid having at least one cis double bond at the 5-position, the 8-position, the 9-position, the 14-position, the 17-position, which has 18 or 20 carbon atoms and a hydroxyl group or carbonyl group at the 12-position, is 12-hydroxy-octadecanoic acid, 12-hydroxy-cis-14-eicosenoic acid, 12-hydroxy-cis-14,cis-17-eicosadienoic acid, 12-hydroxy-cis-8,cis-14-eicosadienoic acid, 12-hydroxy-cis-5,cis-8-eicosadienoic acid, 12-hydroxy-cis-8,cis-14,cis-17-eicosatrienoic acid, 12-hydroxy-cis-5,cis-8,cis-14-eicosatrienoic acid, 12-oxo-octadecanoic acid, 12-oxo-cis-9-octadecenoic acid, 12-oxo-cis-14-eicosenoic acid, 12-oxo-cis-14,cis-17-eicosadienoic acid, 12-oxo-cis-8, cis-14-eicosadienoic acid, 12-oxo-cis-5,cis-8-eicosadienoic acid, 12-oxo-cis-8,cis-14,cis-17-eicosatrienoic acid, or 12-oxo-cis-5,cis-8,cis-14-eicosatrienoic acid, (4) the unsaturated fatty acid having at least one cis double bond at the 5-position, the 8-position, the 11-position, the 17-position, which has 20 carbon atoms and a hydroxyl group or carbonyl group at the 15-position, is 15-hydroxy-cis-11-eicosenoic acid, 15-hydroxy-cis-11,cis-17-eicosadienoic acid, 15-hydroxy-cis-8,cis-11-eicosadienoic acid, 15-hydroxy-cis-5,cis-8,cis-11-eicosatrienoic acid, 15-hydroxy-cis-8,cis-11,cis-17-eicosatrienoic acid, 15-hydroxy-cis-5,cis-11-eicosadienoic acid, 15-hydroxy-cis-5,cis-11,cis-17-eicosatrienoic acid, 15-oxo-cis-11-eicosenoic acid, 15-oxo-cis-11,cis-17-eicosadienoic acid, 15-oxo-cis-8,cis-11-eicosadienoic acid, 15-oxo-cis-5,cis-8,cis-11-eicosatrienoic acid, 15-oxo-cis-8,cis-11,cis-17-eicosatrienoic acid, 15-oxo-cis-5,cis-11-eicosadienoic acid or 15-oxo-cis-5,cis-11,cis-17-eicosatrienoic acid, (5) the saturated fatty acid having 16 carbon atoms and a hydroxyl group or carbonyl group at the 10-position is 10-hydroxy-hexadecanoic acid or 10-oxo-hexadecanoic acid;

[14] the inhibitor of [12], wherein (1) the saturated fatty acid or the unsaturated fatty acid having a trans double bond at the 11-position or at least one cis double bond at the 6-position, the 12-position, which has 18 carbon atoms and a hydroxyl group or carbonyl group at the 10-position, is 10-hydroxy-cis-12-octadecenoic acid, 10-hydroxy-octadecanoic acid, 10-oxo-cis-12-octadecenoic acid, 10-hydroxy-cis-12, cis-15-octadecadienoic acid, 10-hydroxy-cis-6,cis-12-octadecadienoic acid, 10-oxo-cis-12,cis-15-octadecadienoic acid, 10-oxo-cis-6,cis-12-octadecadienoic acid, 10-oxo-trans-11-octadecenoic acid, 10-oxo-trans-11, cis-15-octadecadienoic acid or 10-oxo-cis-6,trans-11-octadecadienoic acid, (2) the saturated fatty acid or the unsaturated fatty acid having at least one cis double bond at the 6-position, the 9-position, the 15-position, which has 18 carbon atoms and a hydroxyl group or carbonyl group at the 13-position, is 13-hydroxy-cis-9-octadecenoic acid, 13-hydroxy-cis-6,cis-9-octadecadienoic acid, 13-hydroxy-cis-9,cis-15-octadecadienoic acid, 10,13-dihydroxy-octadecanoic acid, 10,13-dihydroxy-cis-6-octadecenoic acid, 10,13-dihydroxy-cis-15-octadecenoic acid, 13-oxo-cis-9-octadecenoic acid, 13-oxo-cis-6, cis-9-octadecadienoic acid, or 13-oxo-cis-9,cis-15-octadecadienoic acid, or (3) the saturated fatty acid having 18 carbon atoms and a hydroxyl group at the 12-position is 12-hydroxy-octadecanoic acid;

[15] a method for the prophylaxis or treatment of an inflammatory disease, comprising administering an effective amount of the fatty acid of any one of [1]-[5] to patients;

[16] the method of [15], wherein the inflammatory disease is an inflammatory disease involving macrophage;

[17] the fatty acid of any one of [1]-[5] for use for the prophylaxis or treatment of an inflammatory disease;

[18] the fatty acid of [17], wherein the inflammatory disease is an inflammatory disease involving macrophage;

[19] use of the fatty acid of any one of [1]-[5] in producing a prophylactic or therapeutic agent for an inflammatory disease;

[20] the use of [19], wherein the inflammatory disease is an inflammatory disease involving macrophage.

Effect of the Invention

In the present invention, it was found that hydroxylated fatty acids such as 10-hydroxy-cis-12-octadecenoic acid and 13-hydroxy-cis-9-octadecenoic acid or oxo fatty acids such as 10-oxo-cis-12-octadecenoic acid and 13-oxo-cis-9-octadecenoic acid (hereinafter to be also referred to as rare fatty acid derivative) have an anti-inflammatory action which is a physiological function conventionally not known.

The present invention provides an anti-inflammatory agent containing a rare fatty acid derivative such as hydroxylated fatty acid and the like, based on the function.

were each used at 30 μM. B: Compound No. 11 was used at 10, 20, 30 μM. Nor. shows cells free of an $H_2O_2$ treatment, Con. shows negative control, tBHQ shows positive control, and the vertical axis shows cell survival rate.

Figure 3:
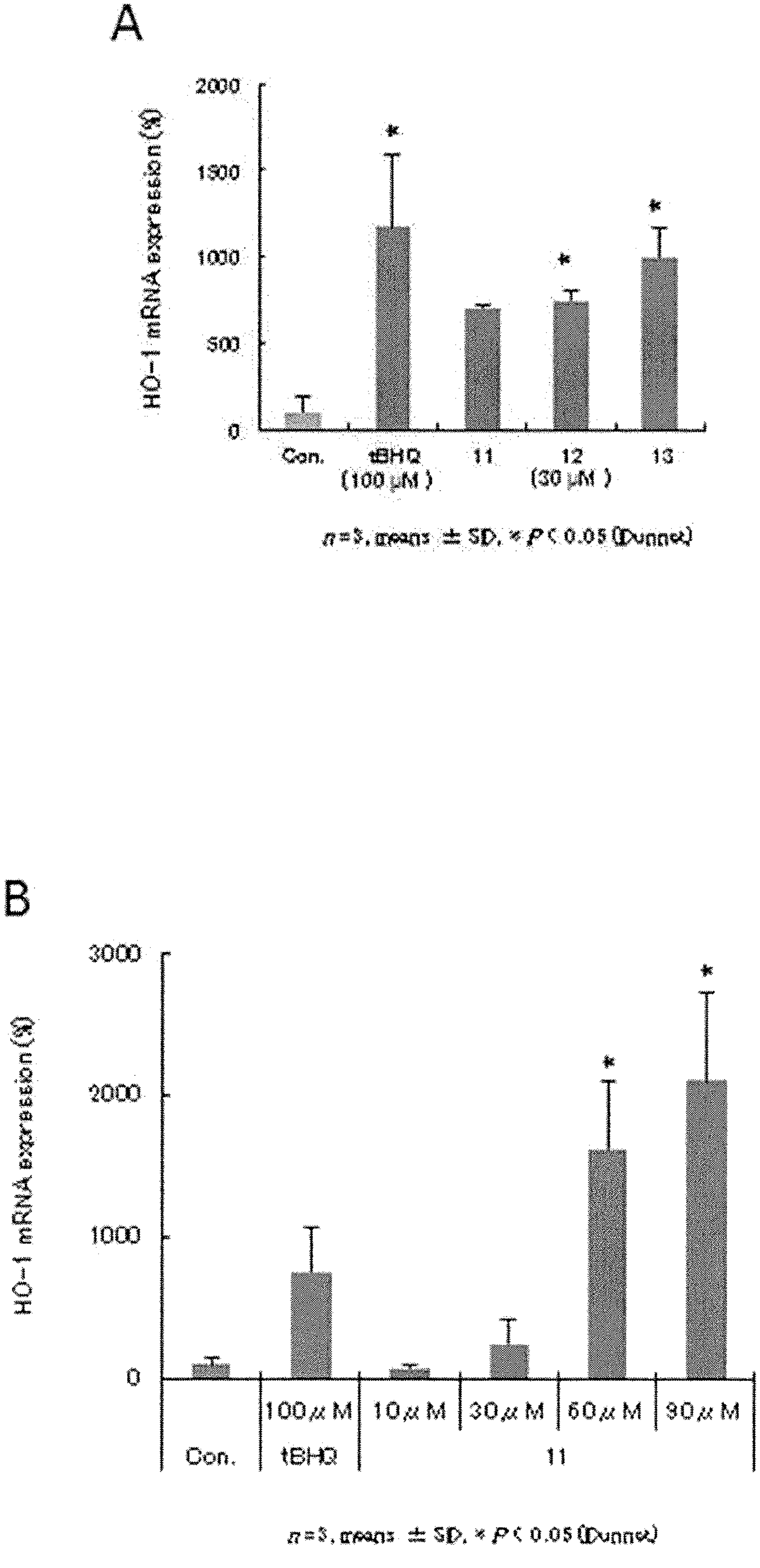

FIG. 3 shows the measurement results of anti-oxidant enzyme HO-1 mRNA expression. A: Various compounds (No. 11-No. 13) were each used at 30 μM. B: Compound No. 11 was used at 10, 30, 60, 90 μM. Con. shows negative control, tBHQ shows positive control, and the vertical axis shows relative expression level of HO-1 mRNA.

Figure 4:
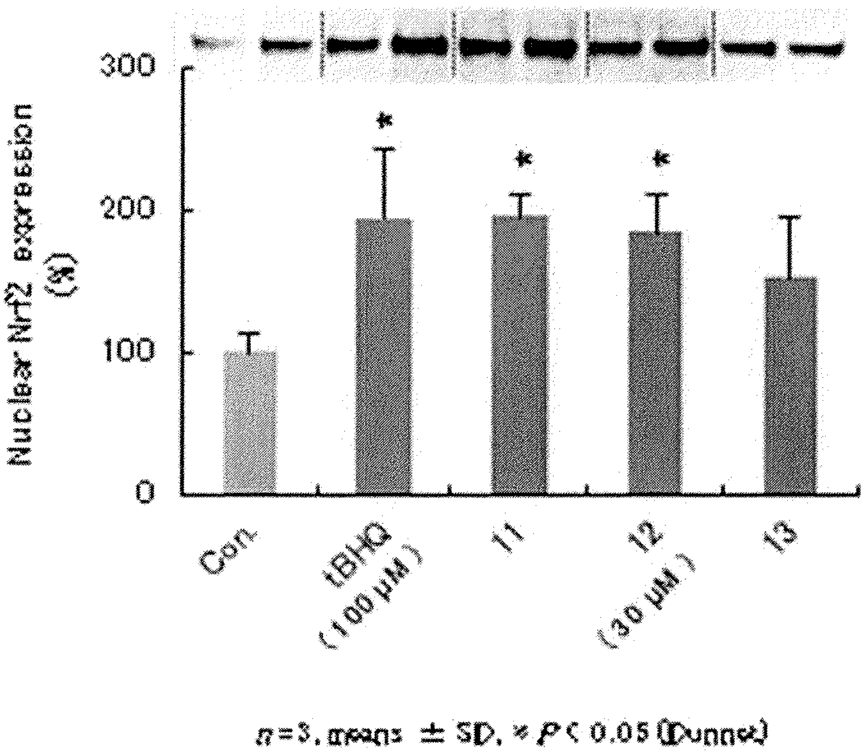

FIG. 4 shows Western blot images and a graph showing the measurement results of intranuclear expression of transcription factor Nrf2. Con. shows negative control, tBHQ shows positive control, and the vertical axis shows relative expression level of intranuclear Nrf2.

Figure 5:
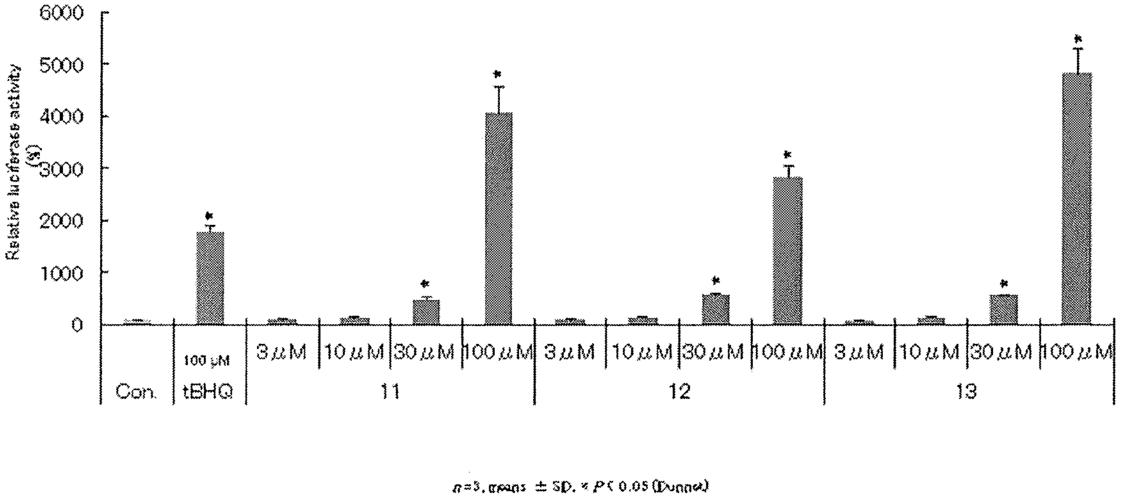

FIG. 5 shows the measurement results of transcription activity of transcription factor Nrf2. Con. shows negative control, tBHQ shows positive control, and the vertical axis shows relative luciferase activity.

Figure 6:
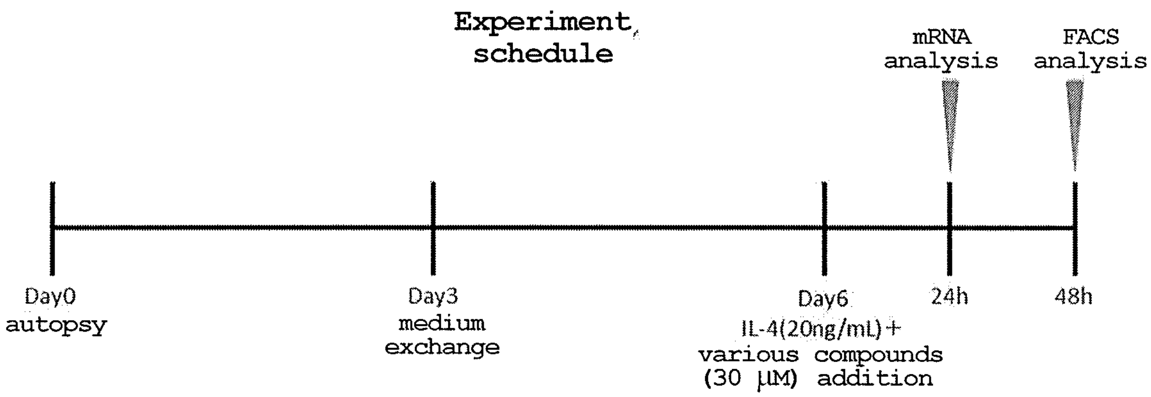

FIG. 6 shows a culture schedule for inducing differentiation of mouse bone marrow-derived cells into M2 macrophage.

Figure 7:
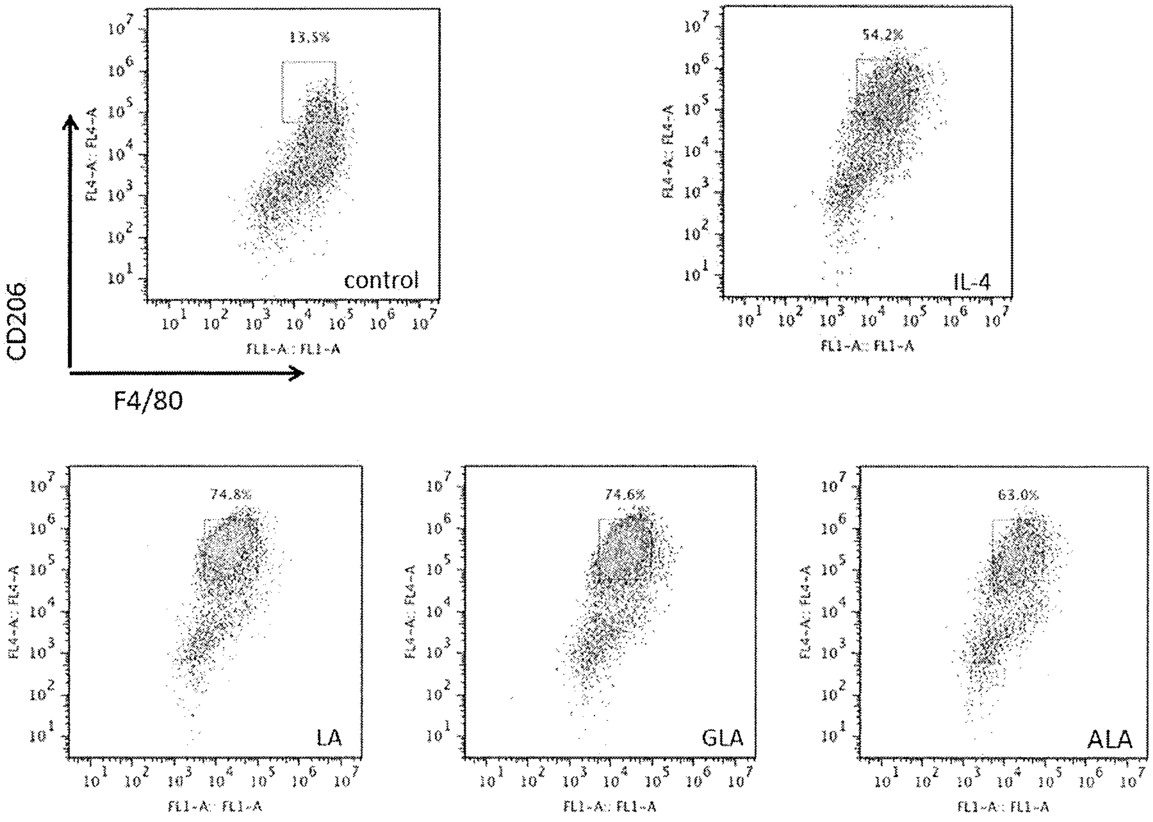

FIG. 7 shows the proportion of cells having cellular surface antigen of M2 macrophage.

Figure 8:
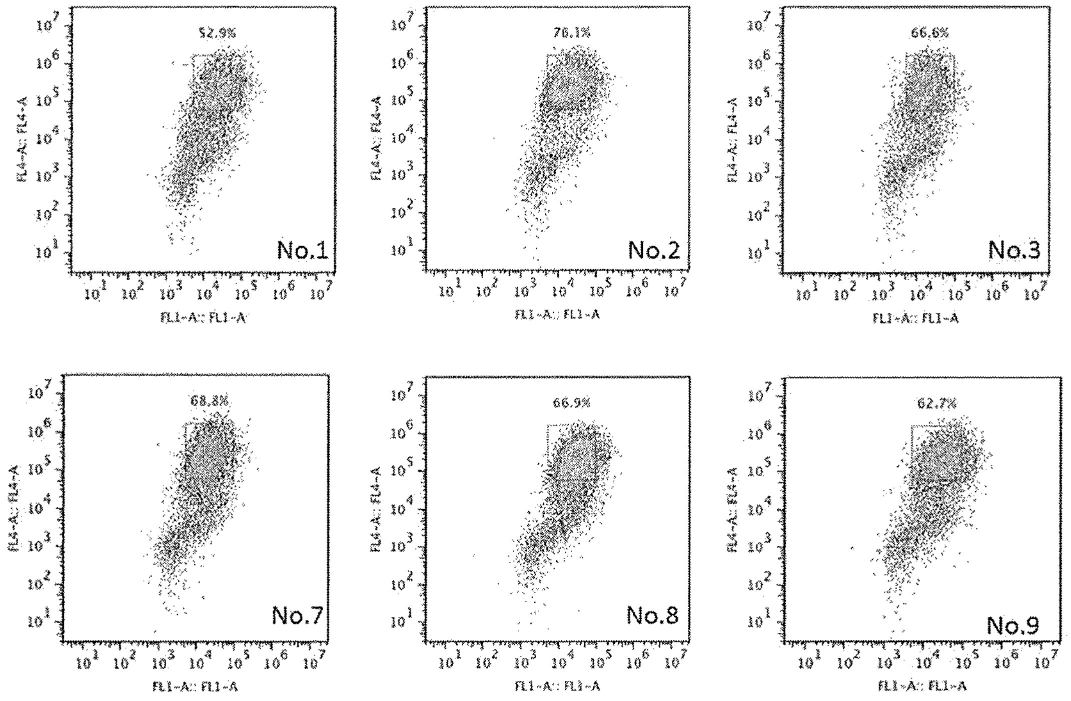

FIG. 8 shows the proportion of cells having cellular surface antigen of M2 macrophage.

Figure 9:
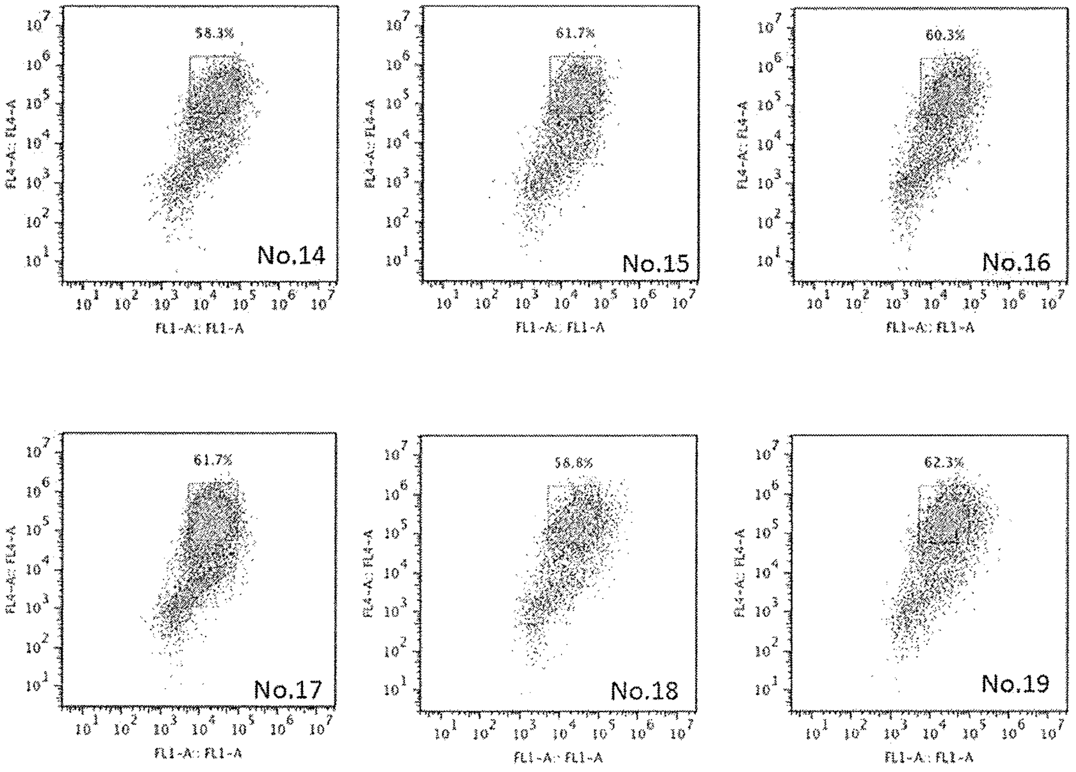

FIG. 9 shows the proportion of cells having cellular surface antigen of M2 macrophage.

Figure 10:
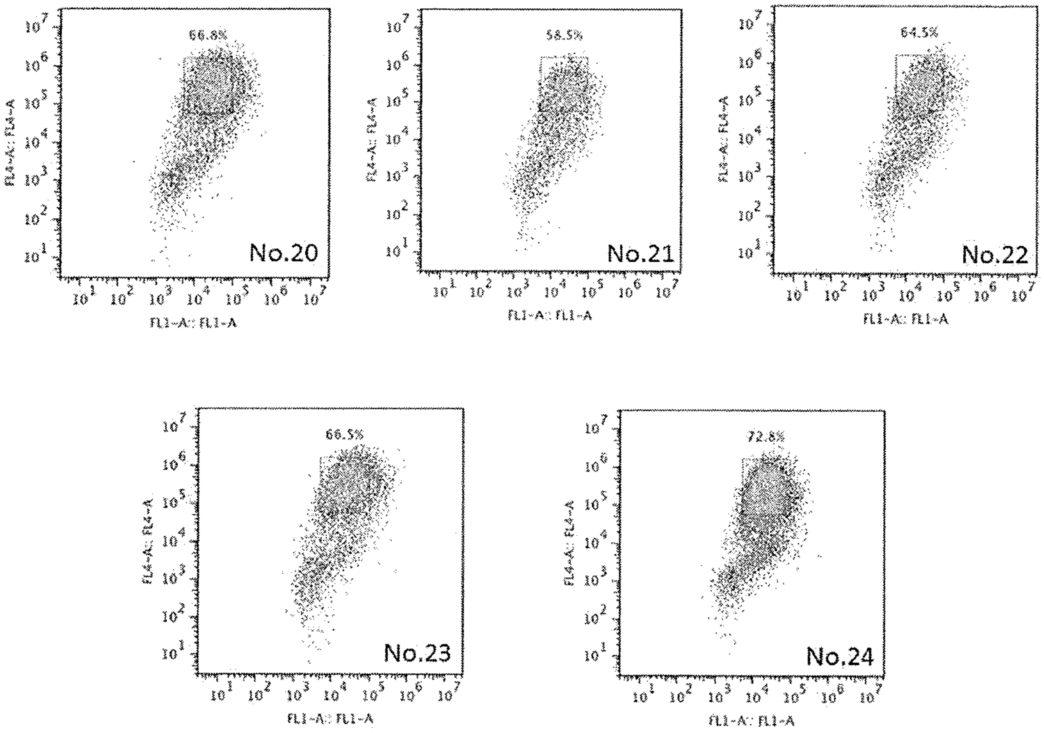

FIG. 10 shows the proportion of cells having cellular surface antigen of M2 macrophage.

Figure 11:
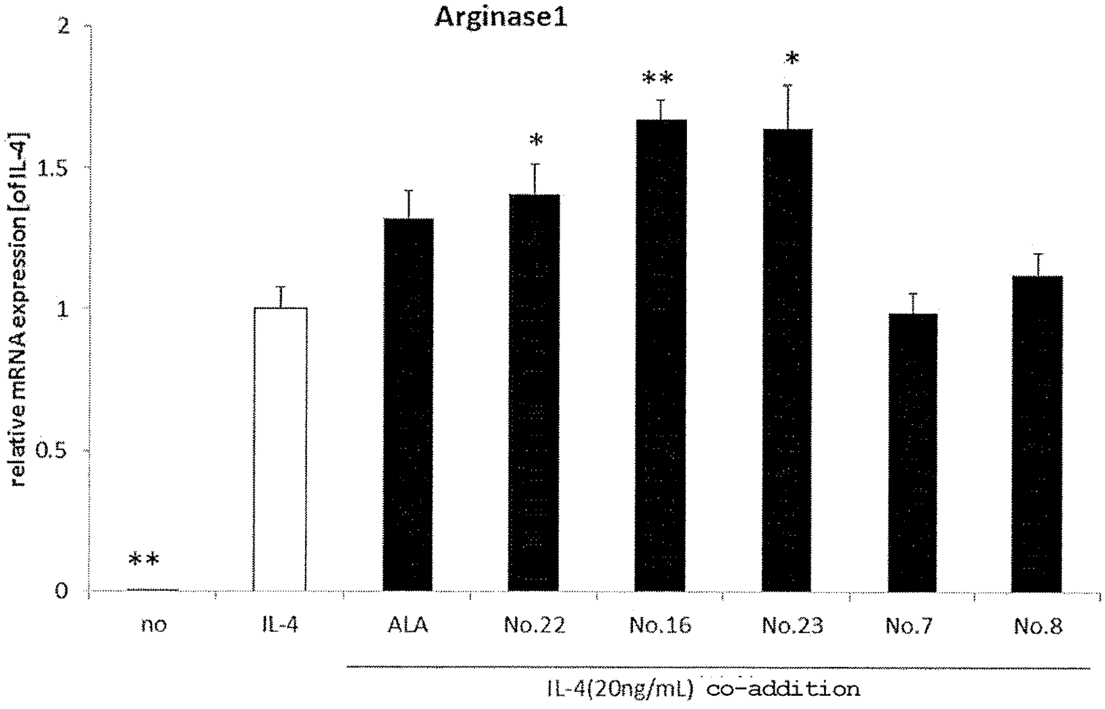

FIG. 11 shows an Arginase 1 mRNA expression level.

Figure 12:
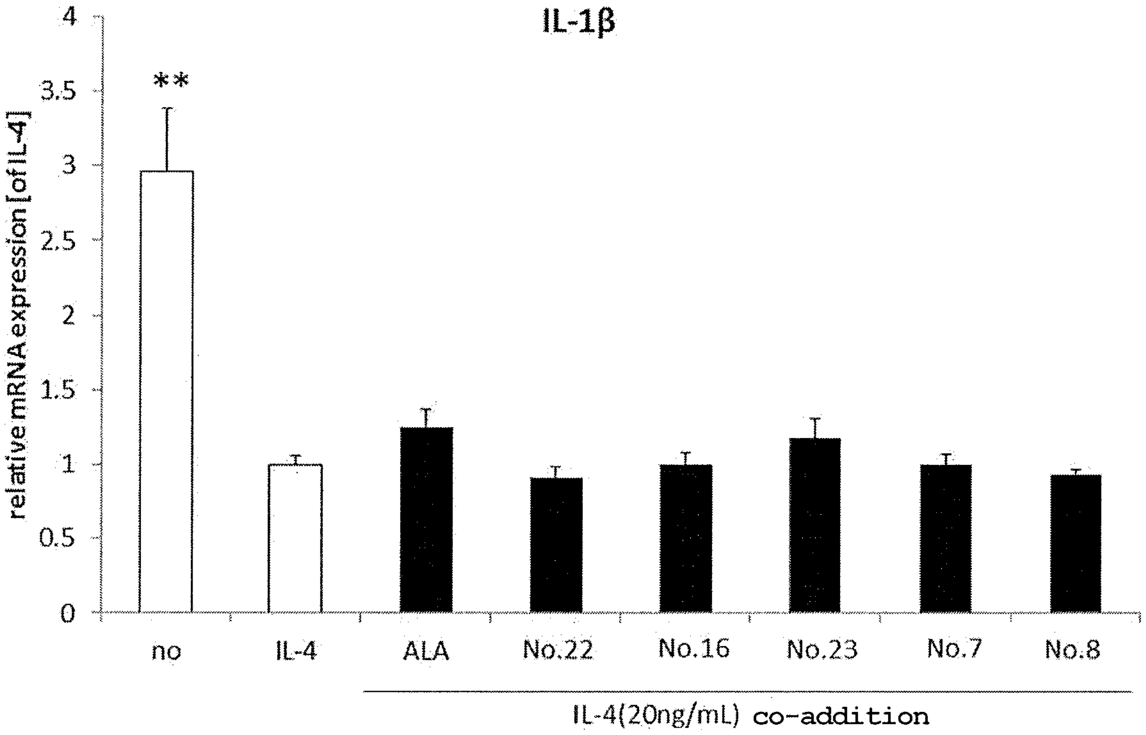

FIG. 12 shows an IL-1β mRNA expression level.

Figure 13:
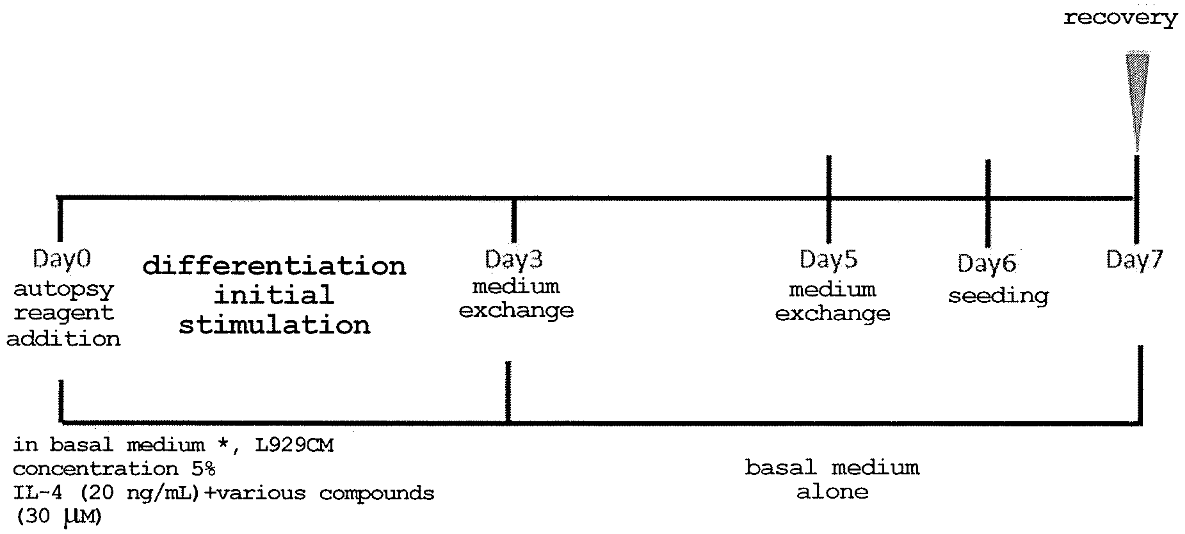

FIG. 13 shows a culture schedule for inducing differentiation of mouse bone marrow-derived cells into M2 macrophage.

Figure 14:
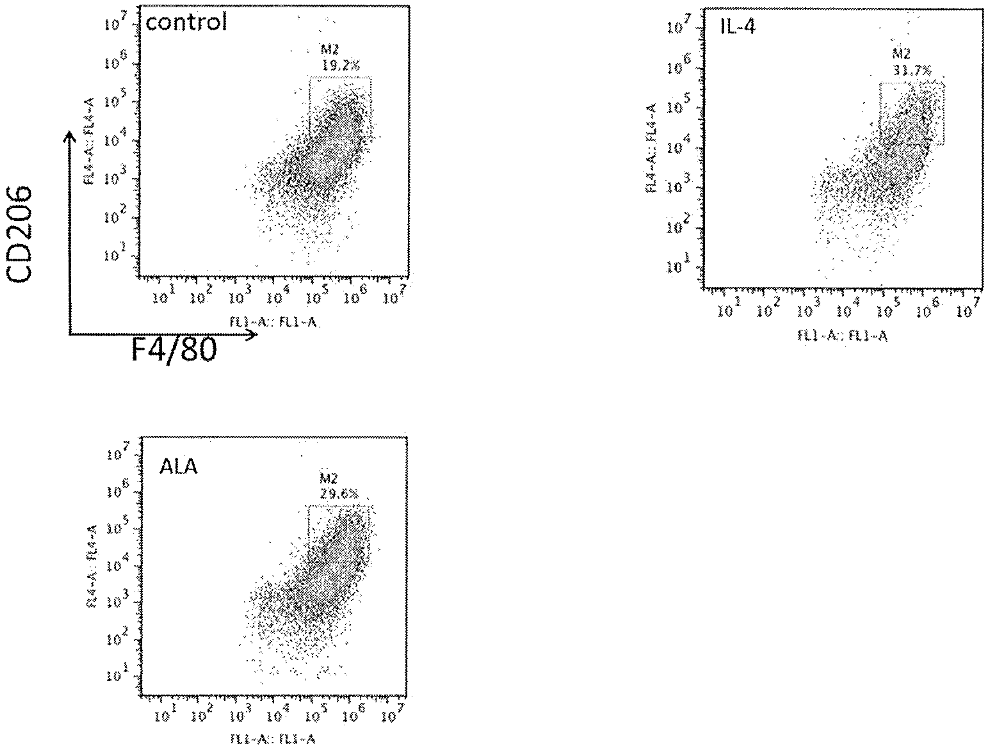

FIG. 14 shows the proportion of cells having cellular surface antigen of M2 macrophage.

Figure 15:
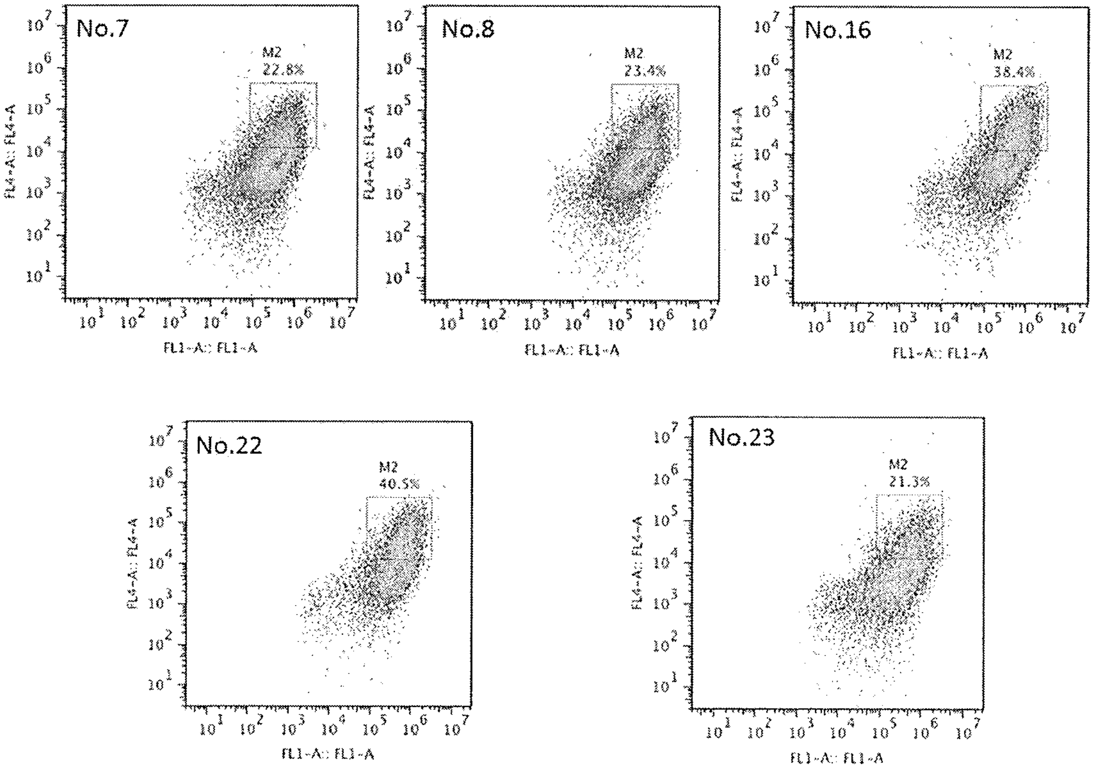

FIG. 15 shows the proportion of cells having cellular surface antigen of M2 macrophage.

Figure 16:
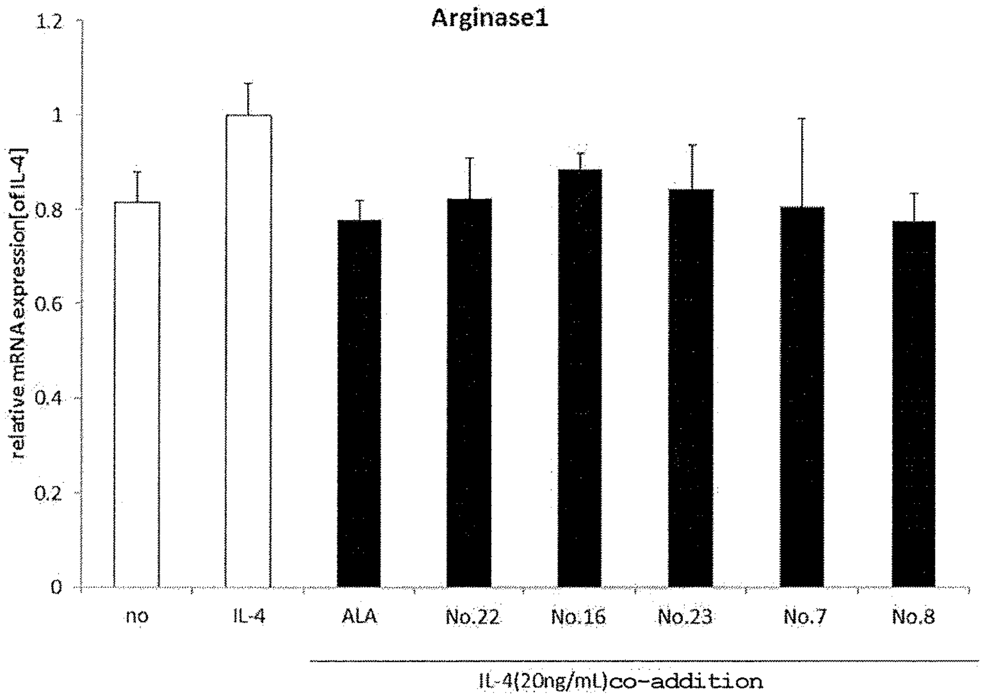

FIG. 16 shows the expression level of Arginase 1 mRNA.

Figure 17:
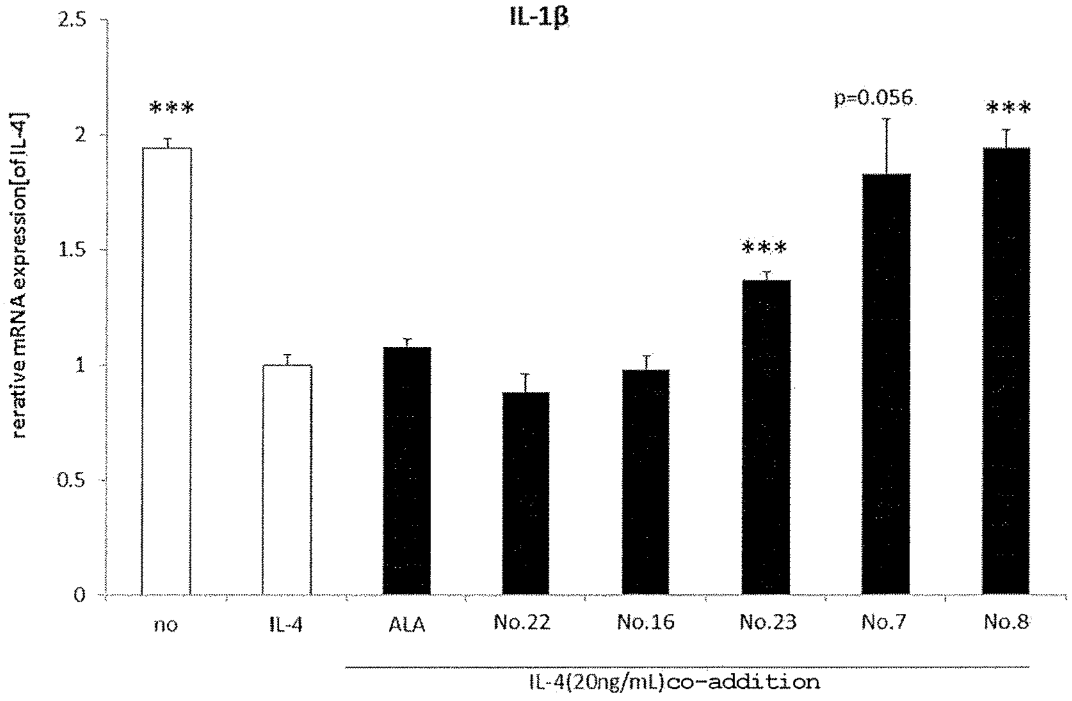

FIG. 17 shows the expression level of IL-1β mRNA.

Figure 18:
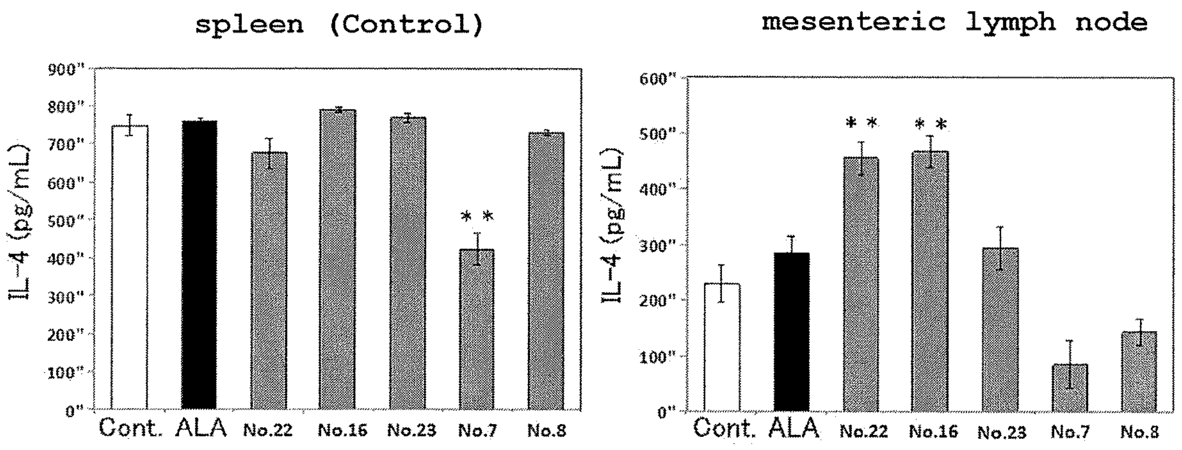

FIG. 18 shows the IL-4 expression level.

Figure 19:
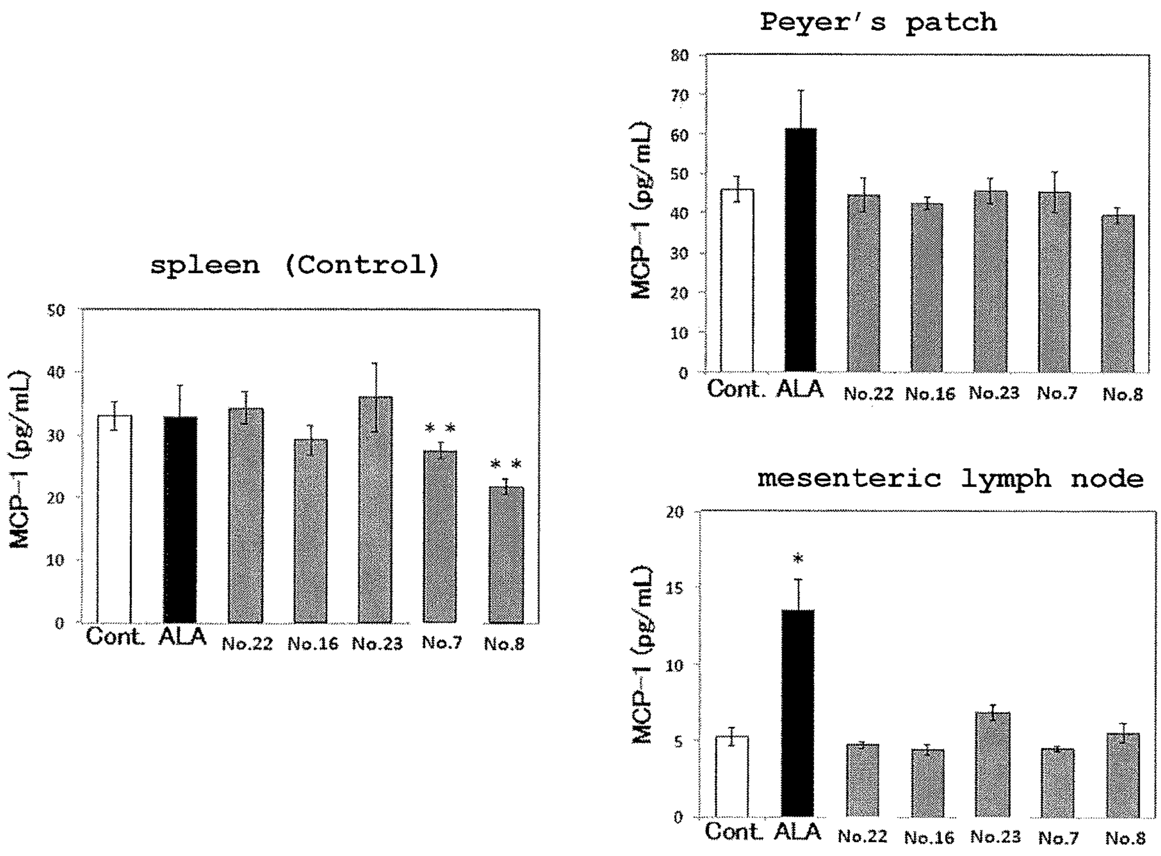

FIG. 19 shows the MCP-1 expression level.

DESCRIPTION OF EMBODIMENTS

The present invention is explained in detail below.

In the present invention, "anti-inflammatory" means suppression of inflammation in vivo. To be specific, an "anti-inflammatory agent" means, for example, prophylaxis and/or suppression of inflammation such as tissue injury (rheumatism, arteriosclerosis etc.) due to allergic disease, chronic inflammation and nerve inflammation disease.

As an index of the above-mentioned anti-inflammatory activity, nitric oxide (NO) production by M1 macrophage can be measured. While macrophage is one kind of immunocyte that plays a central role in the biological defense mechanism against biological exposure to foreign substances such as pathogenic bacteria and the like that invade from the outer world, when macrophage is activated, it becomes M1 macrophage, and produces inflammatory mediators including NO, prostaglandin E2, cytokines such as TNF-α and the like. Promoted production of these inflammatory mediators causes tissue disorders due to chronic inflammation, and induces arteriosclerosis, rheumatism and the like. Therefore, whether NO production by M1 macrophage activated by lipopolysaccharide (LPS) is suppressed by the below-mentioned rare fatty acid derivative of the present invention is confirmed and, when NO production is suppressed, the rare fatty acid derivative can be judged to highly possibly have an anti-inflammatory effect, or have an anti-inflammatory effect. As one example, the NO production amount can be evaluated by the Griess method, though the method is not limited.

As an index of the above-mentioned anti-inflammatory activity, moreover, the cell survival rate relative to $H_2O_2$ can be measured. $H_2O_2$ as an active oxygen promotes production of inflammatory cytokine, and causes inflammatory diseases like the above-mentioned M1 macrophage. Reduction of oxidative stress by $H_2O_2$ affords an anti-inflammatory action. Therefore, whether the survival rate of cultured cells relative to $H_2O_2$ increases by the below-mentioned rare fatty acid derivative of the present invention is confirmed and, when the survival rate increased, the rare fatty acid derivative can be judged to highly possibly have an anti-inflammatory effect, or have an anti-inflammatory effect.

As an index of the above-mentioned anti-inflammatory activity, moreover, promotion of the expression of heme oxygenase (HO-1) can also be measured. HO-1 is an important enzyme as a defense mechanism in the body that protects cells from oxidative stress. Lack of HO-1 promotes cell injury due to oxidative stress, promotes inflammation; on the other hand, promoted expression of HO-1 suppresses oxidative stress, and suppresses inflammation due to cell injury. Therefore, whether the expression of HO-1 in the cultured cells is promoted by the below-mentioned rare fatty acid derivative of the present invention is confirmed and, when the HO-1 expression was promoted, the rare fatty acid derivative can be judged to highly possibly have an anti-inflammatory effect, or have an anti-inflammatory effect.

Alternatively, as an index of the above-mentioned anti-inflammatory activity, promotion of the expression of intranuclear transcription factor Nrf2 can also be measured. The intranuclear expression of Nrf2 is promoted and activated by electrophilic substance, active oxygen, endoplasmic reticulum stress and the like, and Nrf2 controls oxidative stress-adaptive reaction and suppresses inflammation in higher animals. Therefore, whether the intranuclear expression of Nrf2 in the cultured cells is promoted by the below-mentioned rare fatty acid derivative of the present invention is confirmed and, when the intranuclear expression of Nrf2 was promoted, the rare fatty acid derivative can be judged to highly possibly have an anti-inflammatory effect, or have an anti-inflammatory effect. Alternatively, whether the transcription activity of Nrf2 in the cultured cells is promoted by the below-mentioned rare fatty acid derivative of the present invention is confirmed and, when the transcription activity of Nrf2 was promoted, the rare fatty acid derivative can be judged to highly possibly have an anti-inflammatory effect, or have an anti-inflammatory effect.

Alternatively, as an index of the above-mentioned anti-inflammatory activity, an expression marker of M2 macrophage can also be measured. M1 macrophage is activated on infection with bacterium, virus or fungi, and produces a tumor necrosis factor (TNF), nitric oxide, and cytokines such as IL-6, IFN, IL-1β and the like, which are important for the elimination of such pathogens. On the other hand, M2 macrophage is involved in parasitic infection, allergic response, fat metabolism, wound therapy, cancer metastasis and the like. It is known that macrophage is differentiated into M1 or M2, and the proportion of M1 can be decreased by inducing differentiation into M2, as a result of which inflammation is suppressed. Therefore, whether expression of cellular surface antigen expressed in M2 macrophage and expression of mRNA marker expressed in M2 macrophage are promoted by the below-mentioned rare fatty acid derivative of the present invention is confirmed and, when they were promoted, the rare fatty acid derivative can be judged to highly possibly have an anti-inflammatory effect, or have an anti-inflammatory effect.

In the present invention, the rare fatty acid derivative refers to a rare fatty acid derivative that can be produced using a fatty acid saturating enzyme group derived from *Lactobacillus plantarum* and a chemical oxidation reaction (hereinafter sometimes to be abbreviated as "LP-rare fatty acid derivative"), a rare fatty acid derivative that can be produced using a hydration enzyme derived from *Lactobacillus acidophilus* and a chemical oxidation reaction (hereinafter sometimes to be abbreviated as "LA-rare fatty acid derivative"), and 12-oxo-cis-9-octadecenoic acid produced by a chemical oxidation reaction of ricinoleic acid.

The LP-rare fatty acid derivative of the present invention refers to a fatty acid having 18 carbon atoms and a hydroxyl group or carbonyl group at the 10-position. As used herein, the fatty acid having 18 carbon atoms and a hydroxyl group or carbonyl group at the 10-position refers to a hydroxylated fatty acid having 18 carbon atoms and a hydroxyl group at the 10-position (hereinafter sometimes to be abbreviated as "10-hydroxy fatty acid"), or oxo fatty acid having 18 carbon atoms and a carbonyl group at the 10-position (hereinafter sometimes to be abbreviated as "10-oxo fatty acid"). The fatty acid having 18 carbon atoms and a hydroxyl group or carbonyl group at the 10-position may be a saturated fatty acid or an unsaturated fatty acid. When the fatty acid having 18 carbon atoms and a hydroxyl group or carbonyl group at the 10-position is an unsaturated fatty acid, an unsaturated fatty acid having a trans double bond at the 11-position, or at least one cis double bond at the 6-position, the 12-position, the 15-position is preferable. The unsaturated fatty acid may further has a cis double bond at the 6-position or 15-position.

More specifically, while the saturated fatty acid or the unsaturated fatty acid having a trans double bond at the 11-position or at least one cis double bond at the 6-position, the 12-position, the 15-position, which has 18 carbon atoms and a hydroxyl group or carbonyl group at the 10-position (preferably, a saturated fatty acid or an unsaturated fatty acid having a trans double bond at the 11-position or at least one cis double bond at the 6-position, the 12-position, which has 18 carbon atoms and a hydroxyl group or carbonyl group at the 10-position) is not particularly limited, 10-hydroxy-cis-12-octadecenoic acid, 10-hydroxy-cis-12,cis-15-octadecadienoic acid, 10-hydroxy-cis-6,cis-12-octadecadienoic acid, 10-hydroxy-cis-6,cis-12,cis-15-octadecatrienoic acid, 10,12-dihydroxy-octadecanoic acid, 10-hydroxy-octadecanoic acid, 10-hydroxy-cis-15-octadecenoic acid, 10-hydroxy-cis-6-octadecenoic acid, 10-hydroxy-cis-6,cis-15-octadecadienoic acid, 10-hydroxy-trans-11-octadecenoic acid, 10-hydroxy-trans-11,cis-15-octadecadienoic acid, 10-hydroxy-cis-6,trans-11-octadecadienoic acid, 10-hydroxy-cis-6,trans-11,cis-15-octadecatrienoic acid, 10-oxo-cis-12-octadecenoic acid, 10-oxo-cis-12,cis-15-octadecadienoic acid, 10-oxo-cis-6,cis-12-octadecadienoic acid, 10-oxo-cis-6,cis-12,cis-15-octadecatrienoic acid, 10-oxooctadecanoic acid, 10-oxo-cis-6-octadecenoic acid, 10-oxo-cis-15-octadecenoic acid, 10-oxo-cis-6,cis-15-octadecadienoic acid, 10-oxo-trans-11-octadecenoic acid, 10-oxo-cis-6,trans-11-octadecadienoic acid, 10-oxo-trans-11,cis-15-octadecadienoic acid or 10-oxo-cis-6,trans-11,cis-15-octadecatrienoic acid and the like can be mentioned, preferably, 10-hydroxy-cis-12-octadecenoic acid, 10-hydroxy-octadecanoic acid, 10-oxo-cis-12-octadecenoic acid, 10-hydroxy-cis-12,cis-15-octadecadienoic acid, 10-hydroxy-cis-6,cis-12-octadecadienoic acid, 10-oxo-cis-12,cis-15-octadecadienoic acid, 10-oxo-cis-6,cis-12-octadecadienoic acid, 10-oxo-trans-11-octadecenoic acid, 10-oxo-trans-11,cis-15-octadecadienoic acid or 10-oxo-cis-6,trans-11-octadecadienoic acid can be mentioned, more preferably, 10-oxo-trans-11-octadecenoic acid, 10-oxo-trans-11,cis-15-octadecadienoic acid, or 10-oxo-cis-6,trans-11-octadecadienoic acid can be mentioned.

The LA-rare fatty acid derivative in the present invention refers to a fatty acid having 18 carbon atoms and a hydroxyl group or carbonyl group at the 13-position, a fatty acid having 16 carbon atoms and a hydroxyl group or carbonyl group at the 10-position, a fatty acid having 20 carbon atoms and a hydroxyl group or carbonyl group at the 15-position or a fatty acid having 18 or 20 carbon atoms and a hydroxyl group or carbonyl group at the 12-position.

In the present invention, a fatty acid having 18 carbon atoms and a hydroxyl group or carbonyl group at the 13-position refers to a hydroxylated fatty acid having 18 carbon atoms and a hydroxyl group at the 13-position (hereinafter sometimes to be abbreviated as "13-hydroxy fatty acid"), or an oxo fatty acid having 18 carbon atoms and a carbonyl group at the 13-position (hereinafter sometimes to be abbreviated as "13-oxo fatty acid"). As used herein, a fatty acid having 18 carbon atoms and a hydroxyl group or carbonyl group at the 10-position and the 13-position (hereinafter sometimes to be abbreviated as "10,13-dihydroxy fatty acid" or "10,13-dioxo fatty acid"), and a fatty acid having 18 carbon atoms and a hydroxyl group at the 13-position and a carbonyl group at the 10-position (hereinafter sometimes to be abbreviated as "10-oxo-13-hydroxy fatty acid") are also encompassed in one embodiment of the "13-hydroxy fatty acid" or "13-oxo fatty acid". In addition, the fatty acid having 18 carbon atoms and a hydroxyl group or carbonyl group at the 13-position may be a saturated fatty acid or an unsaturated fatty acid. When the fatty acid having 18 carbon atoms and a hydroxyl group or carbonyl group at the 13-position is an unsaturated fatty acid, an unsaturated fatty acid having at least one cis double bond at the 6-position, 9-position, the 15-position is preferable, and an unsaturated fatty acid having a cis double bond at the 9-position is more preferable.

In the present invention, moreover, the fatty acid having 16 carbon atoms and a hydroxyl group or a carbonyl group at the 10-position refers to a hydroxylated fatty acid having 16 carbon atoms and a hydroxyl group at the 10-position (hereinafter sometimes to be abbreviated as "10-hydroxy fatty acid"), or oxo fatty acid having 16 carbon atoms and a carbonyl group at the 10-position (hereinafter sometimes to be abbreviated as "10-oxo fatty acid"). In addition, the fatty acid having 16 carbon atoms and a hydroxyl group or a carbonyl group at the 10-position may be a saturated fatty acid or an unsaturated fatty acid.

In the present invention, the fatty acid having 20 carbon atoms and a hydroxyl group or carbonyl group at the 15-position refers to a hydroxylated fatty acid having 20 carbon atoms and a hydroxyl group at the 15-position (hereinafter sometimes to be abbreviated as "15-hydroxy fatty acid"), or oxo fatty acid having 20 carbon atoms and a carbonyl group at the 15-position fatty acid (hereinafter sometimes to be abbreviated as "15-oxo fatty acid"). In addition, the fatty acid having 20 carbon atoms and a hydroxyl group or carbonyl group at the 15-position may be a saturated fatty acid or an unsaturated fatty acid. When it is an unsaturated fatty acid, an unsaturated fatty acid having at least one cis double bond at the 5-position, the 8-position, the 11-position, the 17-position is preferable.

In the present invention, the fatty acid having 18 or 20 carbon atoms and a hydroxyl group or carbonyl group at the 12-position refers to a hydroxylated fatty acid having 18 or 20 carbon atoms and a hydroxyl group at the 12-position (hereinafter sometimes to be abbreviated as “12-hydroxy fatty acid”), or oxo fatty acid having 18 or 20 carbon atoms and a carbonyl group at the 12-position (hereinafter sometimes to be abbreviated as “12-oxo fatty acid”). In addition, the fatty acid having 18 or 20 carbon atoms and a hydroxyl group or carbonyl group at the 12-position may be a saturated fatty acid or an unsaturated fatty acid. When it is an unsaturated fatty acid, an unsaturated fatty acid having at least one cis double bond at the 5-position, the 8-position, the 9-position, the 14-position, the 17-position is preferable. Also, a saturated fatty acid having 18 carbon atoms and a hydroxyl group at the 12-position is also preferable.

More specifically, while the saturated fatty acid or the unsaturated fatty acid having at least one cis double bond at the 6-position, 9-position, the 15-position, which has 18 carbon atoms and a hydroxyl group or carbonyl group at the 13-position, is not particularly limited, 13-hydroxy-cis-9-octadecenoic acid, 13-hydroxy-cis-6,cis-9-octadecadienoic acid, 13-hydroxy-cis-9,cis-15-octadecadienoic acid, 13-hydroxy-cis-6,cis-9,cis-15-octadecatrienoic acid, 10,13-dihydroxy-octadecanoic acid, 10,13-dihydroxy-cis-6-octadecenoic acid, 10,13-dihydroxy-cis-15-octadecenoic acid, 10,13-dihydroxy-cis-6,cis-15-octadecadienoic acid, 10-oxo-13-hydroxy-octadecanoic acid, 10-oxo-13-hydroxy-cis-6-octadecenoic acid, 10-oxo-13-hydroxy-cis-15-octadecenoic acid, 10-oxo-13-hydroxy-cis-6,cis-15-octadecadienoic acid, 13-hydroxy-cis-5,cis-9-octadecadienoic acid, 13-hydroxy-trans-5,cis-9-octadecadienoic acid, 13-oxo-cis-9-octadecenoic acid, 13-oxo-cis-6,cis-9-octadecadienoic acid, 13-oxo-cis-9,cis-15-octadecadienoic acid, 13-oxo-cis-6,cis-9,cis-15-octadecatrienoic acid, 10,13-dioxo-octadecanoic acid, 10,13-dioxo-cis-6-octadecenoic acid, 10,13-dioxo-cis-15-octadecenoic acid, 10,13-dioxo-cis-6,cis-15-octadecadienoic acid, 13-oxo-cis-5,cis-9-octadecadienoic acid or 13-oxo-trans-5,cis-9-octadecadienoic acid and the like can be mentioned, preferably, 13-hydroxy-cis-9-octadecenoic acid, 13-hydroxy-cis-6,cis-9-octadecadienoic acid, 13-hydroxy-cis-9,cis-15-octadecadienoic acid, 10,13-dihydroxy-octadecanoic acid, 10,13-dihydroxy-cis-6-octadecenoic acid, 10,13-dihydroxy-cis-15-octadecenoic acid, 13-oxo-cis-9-octadecenoic acid, 13-oxo-cis-9,cis-15-octadecadienoic acid, or 13-oxo-cis-6,cis-9-octadecadienoic acid can be mentioned, more preferably, 13-oxo-cis-9,cis-15-octadecadienoic acid or 13-hydroxy-cis-9,cis-15-octadecadienoic acid can be mentioned.

While the saturated fatty acid having 16 carbon atoms and a hydroxyl group or carbonyl group at the 10-position is not particularly limited, 10-hydroxy-hexadecanoic acid or 10-oxo-hexadecanoic acid and the like can be mentioned.

While the unsaturated fatty acid having at least one cis double bond at the 5-position, the 8-position, the 11-position, the 17-position, which has 20 carbon atoms and a hydroxyl group or carbonyl group at the 15-position, is not particularly limited, 15-hydroxy-cis-11-eicosenoic acid, 15-hydroxy-cis-11,cis-17-eicosadienoic acid, 15-hydroxy-cis-8,cis-11-eicosadienoic acid, 15-hydroxy-cis-5,cis-8,cis-11-eicosatrienoic acid, 15-hydroxy-cis-8,cis-11,cis-17-eicosatrienoic acid, 15-hydroxy-cis-5,cis-11-eicosadienoic acid, 15-hydroxy-cis-5,cis-11,cis-17-eicosatrienoic acid, 15-oxo-cis-11-eicosenoic acid, 15-oxo-cis-11,cis-17-eicosadienoic acid, 15-oxo-cis-8,cis-11-eicosadienoic acid, 15-oxo-cis-5,cis-8,cis-11-eicosatrienoic acid, 15-oxo-cis-8,cis-11,cis-17-eicosatrienoic acid, 15-oxo-cis-5,cis-11-eicosadienoic acid or 15-oxo-cis-5,cis-11,cis-17-eicosatrienoic acid and the like can be mentioned.

As the a saturated fatty acid or an unsaturated fatty acid having at least one cis double bond at the 5-position, the 8-position, the 9-position, the 14-position, the 17-position, which has 18 or 20 carbon atoms and a hydroxyl group or carbonyl group at the 12-position (preferably, saturated fatty acid having 18 carbon atoms and a hydroxyl group at the 12-position), 12-hydroxy-octadecanoic acid, 12-hydroxy-cis-14-eicosenoic acid, 12-hydroxy-cis-14,cis-17-eicosadienoic acid, 12-hydroxy-cis-8,cis-14-eicosadienoic acid, 12-hydroxy-cis-5,cis-8-eicosadienoic acid, 12-hydroxy-cis-8,cis-14,cis-17-eicosatrienoic acid, 12-hydroxy-cis-5,cis-8,cis-14-eicosatrienoic acid, 12-oxo-octadecanoic acid, 12-oxo-cis-9-octadecenoic acid, 12-oxo-cis-14-eicosenoic acid, 12-oxo-cis-14,cis-17-eicosadienoic acid, 12-oxo-cis-8,cis-14-eicosadienoic acid, 12-oxo-cis-5,cis-8-eicosadienoic acid, 12-oxo-cis-8,cis-14,cis-17-eicosatrienoic acid, or 12-oxo-cis-5,cis-8,cis-14-eicosatrienoic acid and the like can be mentioned, preferably, 12-hydroxy-octadecanoic acid can be mentioned.

The LP-rare fatty acid derivative to be used in the present invention can be prepared by the method of PCT/JP2012/78747 (WO 2013/168310) found by the inventors. In addition, 10-hydroxy-cis-12-octadecenoic acid can be prepared in reference to Biochemical and Biophysical Research Communications 416 (2011) p. 188-193 and the like. In addition, the LA-rare fatty acid derivative can be prepared by the following method. Alternatively, as 12-hydroxy-octadecanoic acid and the like, commercially available products can be used. 12-Oxo-cis-9-octadecenoic acid can be prepared by a chemical oxidation reaction of a commercially available product of ricinoleic acid.

As the LA-rare fatty acid derivative to be used in the present invention, a hydroxylated fatty acid is produced from an unsaturated fatty acid having 16, 18, 20 carbon atoms by a novel fatty acid hydration enzyme (FA-HY), and an oxo fatty acid can be produced by further oxidizing the hydroxyl group of the hydroxylated fatty acid by an enzyme reaction or chemical reaction.

The above-mentioned novel fatty acid hydration enzyme “FA-HY” is (a) the enzyme protein consisting of the amino acid sequence shown in SEQ ID NO: 2, (b) a protein comprising an amino acid sequence wherein one or plural amino acids in the amino acid sequence shown in SEQ ID NO: 2 are deleted and/or substituted and/or inserted and/or added, and having an enzyme activity that the enzyme protein consisting of the amino acid sequence shown in SEQ ID NO: 2 has, or (c) a protein encoded by a base sequence that hybridizes to a nucleic acid consisting of a chain sequence complementary to the base sequence shown in SEQ ID NO: 1 under stringent conditions, and having an enzyme activity that the enzyme protein consisting of the amino acid sequence shown in SEQ ID NO: 2 has.

More specific examples of the above-mentioned (b) include a protein containing (i) an amino acid sequence which is the amino acid sequence shown in SEQ ID NO: 2, wherein 1-20, preferably 1-10, more preferably 1-several (5, 4, 3 or 2) amino acids are deleted, (ii) an amino acid sequence which is the amino acid sequence shown in SEQ ID NO: 2, wherein 1-20, preferably 1-10, more preferably 1-several number (5, 4, 3 or 2) amino acids are added, (iii) an amino acid sequence which is the amino acid sequence shown in SEQ ID NO: 2, wherein 1-20, preferably 1-10, more preferably 1-several (5, 4, 3 or 2) amino acids are inserted, (iv) an amino acid sequence which is the amino acid sequence shown in SEQ ID NO: 2, wherein 1-20, preferably 1-10, more preferably 1-several (5, 4, 3 or 2) amino acids are substituted by other amino acids, or (v) an amino acid sequence obtained by combining them. When amino acids with similar properties (e.g., glycine and alanine, valine and leucine and isoleucine, serine and threonine, aspartic acid and glutamic acid, asparagine and glutamine, lysine and arginine, cysteine and methionine, phenylalanine and tyrosine etc.) are substituted with each other and the like, a greater number of substitutions and the like are possible.

When amino acids are deleted, substituted or inserted as mentioned above, the positions of deletion, substitution and insertion are not particularly limited as long as the above-mentioned enzyme activity is maintained.

In the above-mentioned (c), the "stringent conditions" are conditions under which nucleotide sequences having high identity, for example, identity of 70, 80, 90, 95 or 99% or above, hybridize to each other and nucleotide sequences having identity lower than that do not hybridize; specifically, conditions of washing once, more preferably 2-3 times, at the salt concentration and temperature corresponding to those in the washing conditions of general Southern hybridization (60° C., 1×SSC, 0.1% SDS, preferably, 0.1×SSC, 0.1% SDS, more preferably, 68° C., 0.1×SSC, 0.1% SDS) and the like.

Reaction 1

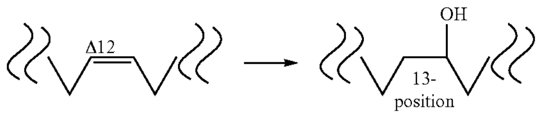

Reaction 2

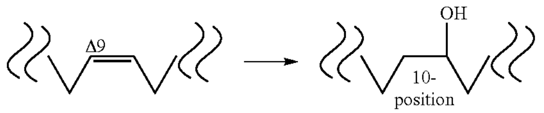

Reaction 3

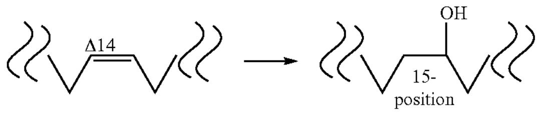

Reaction 4

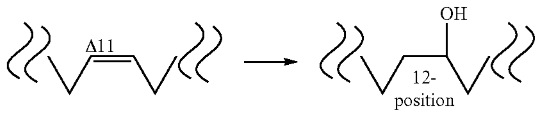

Reaction A

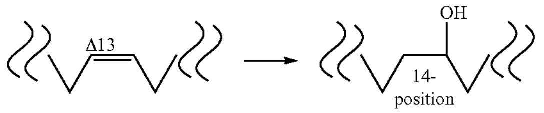

Reaction I

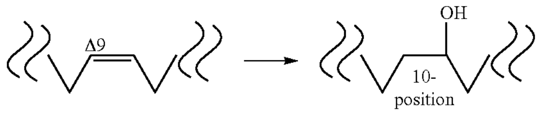

Regarding the above-mentioned (b) or (c), the enzyme activity that the enzyme protein consisting of the amino acid sequence shown in SEQ ID NO: 2 has is not particularly limited as long as it has at least one, preferably all, of (1) an enzyme activity capable of converting an unsaturated fatty acid having 18 carbon atoms and a cis double bond at the 12-position (hereinafter sometimes to be abbreviated as "cis-12 unsaturated fatty acid") utilized as a substrate to a hydroxylated fatty acid having 18 carbon atoms and a hydroxyl group at the 13-position (13-hydroxy fatty acid) (reaction 1), (2) an enzyme activity capable of converting an unsaturated fatty acid having 16 carbon atoms and a cis double bond at the 9-position (hereinafter sometimes to be abbreviated as "cis-9 unsaturated fatty acid")) utilized as a substrate to a hydroxylated fatty acid having 16 carbon atoms and a hydroxyl group at the 10-position (10-hydroxy fatty acid) (reaction 2), (3) an enzyme activity capable of converting an unsaturated fatty acid having carbon atoms and a cis double bond at the 14-position (hereinafter sometimes to be abbreviated as "cis-14 unsaturated fatty acid")) utilized as a substrate to a hydroxylated fatty acid having 20 carbon atoms and a hydroxyl group at the 15-position (15-hydroxy fatty acid) (reaction 3), (4) an enzyme activity capable of converting an unsaturated fatty acid having 18 or 20 carbon atoms and a cis double bond at the 11-position (hereinafter sometimes to be abbreviated as "cis-11 unsaturated fatty acid")) utilized as a substrate to a hydroxylated fatty acid having 18 or 20 carbon atoms and a hydroxyl group at the 12-position (12-hydroxy fatty acid) (reaction 4), an enzyme activity capable of converting cis-4,cis-7,cis-10, cis-13,cis-16,cis-19-docosahexaenoic acid (DHA) to 14-hydroxy-cis-4,cis-7,cis-10,cis-16,cis-19-docosapentaenoic acid (reaction A), and an enzyme activity capable of converting cis-9-tetradecenoic acid (myristoleic acid) to 10-hydroxy-tetradecanoic acid (reaction I).

The above-mentioned "cis-12 unsaturated fatty acid", "cis-9 unsaturated fatty acid", "cis-14 unsaturated fatty acid", and "cis-11 unsaturated fatty acid" are not particularly limited as long as they are an unsaturated fatty acid having 18 carbon atoms and a cis double bond at the 12-position, an unsaturated fatty acid having 16 carbon atoms and a cis double bond at the 9-position, an unsaturated fatty acid having 20 carbon atoms and a cis double bond at the 14-position, an unsaturated fatty acid having 18 or 20 carbon atoms and a cis double bond at the 11-position, respectively and, for example, monovalent unsaturated fatty acid, divalent unsaturated fatty acid, trivalent unsaturated fatty acid, tetravalent unsaturated fatty acid, pentavalent unsaturated fatty acid and the like can be mentioned. In the present specification, the "fatty acid" encompasses not only free acids but also ester form, salt with basic compound and the like. The "DHA" and "myristoleic acid" also encompass not only free acids but also ester form, salt with basic compound and the like.

The above-mentioned FA-HY can be isolated from, for example, the fungus, culture medium of *Lactobacillus acidophilus* by a protein separation and purification technique known per se. Alternatively, FA-HY may be used as the fungus of *Lactobacillus acidophilus* containing FA-HY or fungal debris thereof. The fungus of *Lactobacillus acidophilus* containing FA-HY is not particularly limited as long as it contains the above-mentioned FA-HY and, for example, NITE BP-01788 deposited on Jan. 17, 2014 at the NITE Patent Microorganisms Depositary (NPMD) and the like can be mentioned. Alternatively, FA-HY can also be produced as a recombinant protein by isolating a gene encoding FA-HY, subcloning same into a suitable vector, introducing same into a suitable host such as *Escherichia coli* and the like and culturing same. FA-HY may be a purified one or a crudely purified one. Alternatively, hydratase may be expressed in fungus such as *Escherichia coli* and the like and the fungus itself may be used or culture medium thereof may be used. Furthermore, the enzyme may be of a free form, or immobilized by various carriers.

As a vector containing a nucleic acid encoding the above-mentioned FA-HY, one suitable for a host cell to be introduced with the vector may be appropriately selected according to the object (e.g., protein expression) and can be used. In the case of an expression vector, it contains the nucleic acid of the present invention, which is operably linked to an appropriate promoter, and preferably contains a transcription termination signal, i.e., terminator region, at the downstream of the nucleic acid of the present invention. Furthermore, it can also contain a selection marker gene for selection of a transformant (drug resistance gene, gene that complements auxotrophic mutation etc.). Also, it may contain a sequence encoding a tag sequence useful for separation and purification of the expressed protein and the like. In addition, the vector may be incorporated into the genome of a target host cell. The vector of the present invention can be introduced into a target host cell by a transformation method known per se such as a competent cell method, a protoplast method, a calcium phosphate coprecipitation method and the like.

In the present specification, the "host cell" may be any cell as long as it can express a vector containing a nucleic acid encoding the above-mentioned FA-HY, and bacterium, yeast, fungi, higher eukaryotic cell and the like can be mentioned. Examples of the bacterium include gram-positive bacteria such as *bacillus, Streptomyces* and the like and gram negative bacteria such as *Escherichia coli* and the like. A recombinant cell introduced with a vector containing a nucleic acid encoding FA-HY can be cultivated by a method known per se which is suitable for the host cell.

"Purification" of the above-mentioned FA-HY can be performed by a method known per se, for example, fungi collected by centrifugation and the like are ruptured by ultrasonication or glass beads and the like, solid such as cell debris is removed by centrifugation and the like, and the like to give a crude enzyme solution, which is subjected to a salting out method using ammonium sulfate, sodium sulfate and the like, chromatographys such as ion exchange chromatography, gel filtration chromatography, affinity chromatography and the like, gel electrophoresis and the like.

The above-mentioned FA-HY has, as mentioned above, an enzyme activity capable of converting cis-12 unsaturated fatty acid, cis-9 unsaturated fatty acid, cis-14 unsaturated fatty acid, cis-11 unsaturated fatty acid, DHA, myristoleic acid utilized as substrates to 13-hydroxy fatty acid, 10-hydroxy fatty acid, 15-hydroxy fatty acid, 12-hydroxy fatty acid, 14-hydroxy-cis-4,cis-7,cis-10,cis-16,cis-19-docosapentaenoic acid, 10-hydroxy-tetradecanoic acid, respectively. Therefore, the present invention also provides [1] a method of producing 13-hydroxy fatty acid from cis-12 unsaturated fatty acid by a hydration reaction using the above-mentioned FA-HY (production method 1), [2] a method of producing 10-hydroxy fatty acid from cis-9 unsaturated fatty acid by a hydration reaction using the above-mentioned FA-HY (production method 2), [3] a method of producing 15-hydroxy fatty acid from cis-14 unsaturated fatty acid by a hydration reaction using the above-mentioned FA-HY (production method 3), [4] a method of producing 12-hydroxy fatty acid from cis-11 unsaturated fatty acid by a hydration reaction using the above-mentioned FA-HY (production method 4), [A] a method of producing 14-hydroxy-cis-4,cis-7,cis-10,cis-16,cis-19-docosapentaenoic acid from DHA by a hydration reaction using the above-mentioned FA-HY (production method A), and [I] a method of producing 10-hydroxy-tetradecanoic acid from myristoleic acid by a hydration reaction using the FA-HY of the present invention (production method I).

Examples of the "cis-12 unsaturated fatty acid" in the above-mentioned production method 1 include cis-9,cis-12-octadecadienoic acid (linoleic acid), cis-6,cis-9,cis-12-octadecatrienoic acid (γ-linolenic acid), cis-9,cis-12,cis-15-octadecatrienoic acid (α-linolenic acid), cis-6,cis-9,cis-12,cis-15-octadecatetraenoic acid (stearidonic acid), as well as 10-hydroxy-cis-12-octadecenoic acid, 10-hydroxy-cis-6,cis-12-octadecadienoic acid, 10-hydroxy-cis-12,cis-15-octadecadienoic acid, 10-hydroxy-cis-6,cis-12,cis-15-octadecatrienoic acid, 10-oxo-cis-12-octadecenoic acid, 10-oxo-cis-6,cis-12-octadecadienoic acid, 10-oxo-cis-12,cis-15-octadecadienoic acid, 10-oxo-cis-6,cis-12,cis-15-octadecatrienoic acid, cis-5,cis-9,cis-12-octadecatrienoic acid(pinolenic acid), trans-5,cis-9,cis-12-octadecatrienoic acid (columbinic acid), which are now producible by WO 2013/168310, and the like. These substrates may be obtained by a method other than WO 2013/168310.

Examples of the "13-hydroxy fatty acid" produced by the above-mentioned production method 1 include 13-hydroxy-cis-9-octadecenoic acid induced from cis-9,cis-12-octadecadienoic acid (linoleic acid), 13-hydroxy-cis-6,cis-9-octadecadienoic acid induced from cis-6,cis-9,cis-12-octadecatrienoic acid (γ-linolenic acid), 13-hydroxy-cis-9,cis-15-octadecadienoic acid induced from cis-9,cis-12,cis-15-octadecatrienoic acid (α-linolenic acid), 13-hydroxy-cis-6,cis-9,cis-15-octadecatrienoic acid induced from cis-6,cis-9,cis-12,cis-15-octadecatetraenoic acid (stearidonic acid), 10,13-dihydroxy-octadecanoic acid induced from 10-hydroxy-cis-12-octadecenoic acid, 10,13-dihydroxy-cis-6-octadecenoic acid induced from 10-hydroxy-cis-6,cis-12-octadecadienoic acid, 10,13-dihydroxy-cis-15-octadecenoic acid induced from 10-hydroxy-cis-12,cis-15-octadecadienoic acid, 10,13-dihydroxy-cis-6,cis-15-octadecadienoic acid induced from 10-hydroxy-cis-6,cis-12,cis-15-octadecatrienoic acid, 10-oxo-13-hydroxy-octadecanoic acid induced from 10-oxo-cis-12-octadecenoic acid, 10-oxo-13-hydroxy-cis-6-octadecenoic acid induced from 10-oxo-cis-6,cis-12-octadecadienoic acid, 10-oxo-13-hydroxy-cis-15-octadecenoic acid induced from 10-oxo-cis-12,cis-15-octadecadienoic acid, 10-oxo-13-hydroxy-cis-6,cis-15-octadecadienoic acid induced from 10-oxo-cis-6,cis-12,cis-15-octadecatrienoic acid, 13-hydroxy-cis-5,cis-9-octadecadienoic acid induced from cis-5,cis-9,cis-12-octadecatrienoic acid (pinolenic acid), 13-hydroxy-trans-5,cis-9-octadecadienoic acid induced from trans-5,cis-9,cis-12-octadecatrienoic acid (columbinic acid) and the like.

Examples of the "cis-9 unsaturated fatty acid" in the above-mentioned production method 2 include cis-9-hexadecenoic acid (pulmitoleic acid) and the like.

Examples of the "10-hydroxy fatty acid" produced by the above-mentioned production method 2 include 10-hydroxy-hexadecanoic acid induced from cis-9-hexadecenoic acid (pulmitoleic acid) and the like.

Examples of the "cis-14 unsaturated fatty acid" in the above-mentioned production method 3 include cis-11,cis-14-eicosadienoic acid, cis-11,cis-14,cis-17-eicosatrienoic acid, cis-8,cis-11,cis-14-eicosatrienoic acid (dihomo-γ-linolenic acid), cis-5,cis-8,cis-11,cis-14-eicosatetraenoic acid (arachidonic acid), cis-8,cis-11,cis-14,cis-17-eicosatetraenoic acid, cis-5,cis-11,cis-14-eicosatrienoic acid (sciadonic acid), cis-5,cis-11,cis-14,cis-17-eicosatetraenoic acid (juniperonic acid) and the like.

Examples of the "15-hydroxy fatty acid" produced by the above-mentioned production method 3 include 15-hydroxy-cis-11-eicosenoic acid induced from cis-11,cis-14-eicosadienoic acid, 15-hydroxy-cis-11,cis-17-eicosadienoic acid induced from cis-11,cis-14,cis-17-eicosatrienoic acid, 15-hydroxy-cis-8, cis-11-eicosadienoic acid induced from cis-8,cis-11,cis-14-eicosatrienoic acid (dihomo-γ-linolenic acid), 15-hydroxy-cis-5,cis-8,cis-11-eicosatrienoic acid induced from cis-5,cis-8,cis-11,cis-14-eicosatetraenoic acid (arachidonic acid), 15-hydroxy-cis-8,cis-11,cis-17-eicosatrienoic acid induced from cis-8,cis-11,cis-14,cis-17-eicosatetraenoic acid, 15-hydroxy-cis-5,cis-11-eicosadienoic acid induced from cis-5,cis-11,cis-14-eicosatrienoic acid (sciadonic acid), 15-hydroxy-cis-5,cis-11,cis-17-eicosatrienoic acid induced from cis-5,cis-11,cis-14,cis-17-eicosatetraenoic acid (juniperonic acid) and the like.

Examples of the "cis-11 unsaturated fatty acid" in the above-mentioned production method 4 include cis-11-octadecenoic acid (cis-vaccenic acid), cis-11,cis-14-eicosadienoic acid, cis-11,cis-14,cis-17-eicosatrienoic acid, cis-8, cis-11,cis-14-eicosatrienoic acid (dihomo-γ-linolenic acid), cis-5,cis-8,cis-11-eicosatrienoic acid (mead acid), cis-8,cis-11,cis-14,cis-17-eicosatetraenoic acid, cis-5,cis-8,cis-11,cis-14-eicosatetraenoic acid (arachidonic acid) and the like.

Examples of the "12-hydroxy fatty acid" produced by the above-mentioned production method 4 include 12-hydroxy-octadecanoic acid induced from cis-11-octadecenoic acid (cis-vaccenic acid), 12-hydroxy-cis-14-eicosenoic acid induced from cis-11,cis-14-eicosadienoic acid, 12-hydroxy-cis-14,cis-17-eicosadienoic acid induced from cis-11,cis-14, cis-17-eicosatrienoic acid, 12-hydroxy-cis-8,cis-14-eicosadienoic acid induced from cis-8,cis-11,cis-14-eicosatrienoic acid (dihomo-γ-linolenic acid), 12-hydroxy-cis-5,cis-8-eicosadienoic acid induced from cis-5,cis-8,cis-11-eicosatrienoic acid (mead acid), 12-hydroxy-cis-8,cis-14,cis-17-eicosatrienoic acid induced from cis-8,cis-11,cis-14,cis-17-eicosatetraenoic acid, 12-hydroxy-cis-5,cis-8,cis-14-eicosatrienoic acid induced from cis-5,cis-8,cis-11,cis-14-eicosatetraenoic acid (arachidonic acid) and the like.

The hydration reaction may be performed in a suitable buffer (e.g., phosphate buffer, tris buffer, borate buffer etc.) by mixing unsaturated fatty acid, which is a substrate, and the above-mentioned FA-HY at suitable concentrations and incubating the mixture. The substrate concentration is, for example, 1-1000 g/L, preferably 10-500 g/L, more preferably 20-250 g/L. The amount of the above-mentioned FA-HY to be added is, for example, 0.001-10 mg/mL, preferably 0.1-5 mg/mL, more preferably 0.2-2 mg/mL.

A "cofactor" may be used for a hydration reaction (reaction 1-4, reaction A or reaction I) and, for example, FAD and the like can be used. The concentration of addition may be any as long as the hydration reaction proceeds efficiently. It is preferably 0.001-20 mM, more preferably 0.01-10 mM.

Furthermore, an "activator" may be used for the hydration reaction and, for example, 1 or 2 compounds selected from the group consisting of NADH and NADPH can be mentioned. The concentration of addition thereof may be any as long as the hydration reaction proceeds efficiently. It is preferably 0.1-20 mM, more preferably 1-10 mM.

The hydration reaction is desirably performed at a preferable temperature and in a preferable pH range for the above-mentioned FA-HY. For example, the reaction temperature is 5-50° C., preferably 20-45° C. The pH of the reaction mixture is, for example, pH 4-10, preferably pH 5-9. The reaction time is not particularly limited and it is, for example, 10 min-72 hr, preferably 30 min-36 hr.

In one preferable embodiment of the present invention, the above-mentioned FA-HY is provided to the reaction system in the form of recombinant cells (e.g., *Escherichia coli, Bacillus subtilis*, yeast, insect cell, animal cell etc.) introduced with an expression vector containing a nucleic acid encoding same. In this case, the hydration reaction can also be performed by cultivating the cells in a liquid medium suitable for the culture of the cells and added with cofactor and a substrate and, where necessary, an activator.

Reaction 5

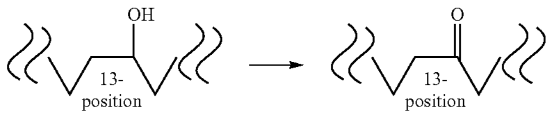

Reaction 6

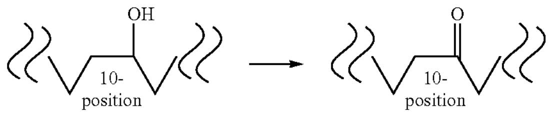

Reaction 7

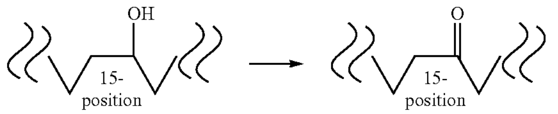

Reaction 8

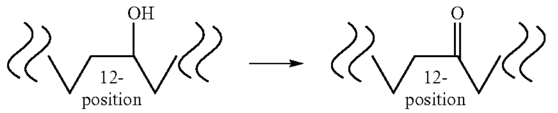

Reaction B

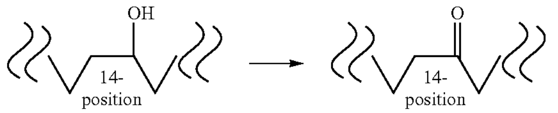

Reaction II

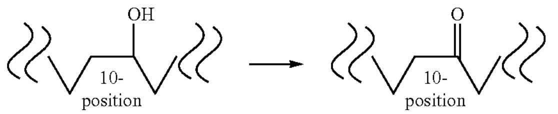

Furthermore, by a dehydrogenation reaction or chemical oxidation using chrome acid, an oxo fatty acid having 18 carbon atoms and a carbonyl group at the 13-position (hereinafter sometimes to be abbreviated as "13-oxo fatty acid") is produced from 13-hydroxy fatty acid obtained in the above-mentioned production methods 1-4, production method A, production method I (reaction 5), an oxo fatty acid having 16 carbon atoms and a carbonyl group at the 10-position (hereinafter sometimes to be abbreviated as "10-oxo fatty acid") is produced from 10-hydroxy fatty acid (reaction 6), an oxo fatty acid having 20 carbon atoms and a carbonyl group at the 15-position (hereinafter sometimes to be abbreviated as "15-oxo fatty acid") is produced from 15-hydroxy fatty acid (reaction 7), an oxo fatty acid having 18 or 20 carbon atoms and a carbonyl group at the 12-position (hereinafter sometimes to be abbreviated as "12-oxo fatty acid") is produced from 12-hydroxy fatty acid (reaction 8), 14-oxo-cis-4,cis-7,cis-10,cis-16,cis-19-docosapentaenoic acid is produced from 14-hydroxy-cis-4,cis-7,cis-10,cis-16,cis-19-docosapentaenoic acid (reaction B), and 10-oxo-tetradecanoic acid is produced from 10-hydroxy-tetradecanoic acid (reaction II).

Therefore, [5] a method of producing 13-oxo fatty acid, comprising subjecting cis-12 unsaturated fatty acid to a hydration reaction using the above-mentioned FA-HY to induce 13-hydroxy fatty acid, and subjecting the 13-hydroxy fatty acid to a dehydrogenation reaction or chemical oxidation (production method 5), [6] a method of producing 10-oxo fatty acid, comprising subjecting cis-9 unsaturated fatty acid to a hydration reaction using the above-mentioned FA-HY to induce 10-hydroxy fatty acid, and subjecting the 10-hydroxy fatty acid to a dehydrogenation reaction or chemical oxidation (production method 6), [7] a method of producing 15-oxo fatty acid, comprising subjecting cis-14 unsaturated fatty acid to a hydration reaction using the above-mentioned FA-HY to induce 15-hydroxy fatty acid, and subjecting the 15-hydroxy fatty acid to a dehydrogenation reaction or chemical oxidation (production method 7), [8] a method of producing 12-oxo fatty acid, comprising subjecting cis-11 unsaturated fatty acid to a hydration reaction using the above-mentioned FA-HY to induce 12-hydroxy fatty acid, and subjecting the 12-hydroxy fatty acid to a dehydrogenation reaction or chemical oxidation (production method 8), [B] a method of producing 14-oxo-cis-4,cis-7,cis-10,cis-16,cis-19-docosapentaenoic acid, comprising subjecting DHA to a hydration reaction using the FA-HY of the present invention to induce 14-hydroxy-cis-4,cis-7,cis-10,cis-16,cis-19-docosapentaenoic acid, and subjecting the 14-hydroxy-cis-4,cis-7,cis-10,cis-16,cis-19-docosapentaenoic acid to a dehydrogenation reaction or chemical oxidation (production method B), and [II] a method of producing 10-oxo-tetradecanoic acid, comprising subjecting myristoleic acid to a hydration reaction using the FA-HY of the present invention to induce 10-hydroxy-tetradecanoic acid, and subjecting the 10-hydroxy-tetradecanoic acid to a dehydrogenation reaction or chemical oxidation (production method II) are provided.

The "cis-12 unsaturated fatty acid", "cis-9 unsaturated fatty acid", "cis-14 unsaturated fatty acid", "cis-11 unsaturated fatty acid" in the above-mentioned production methods 5-8 are the same as the substrates in the above-mentioned production methods 1-4.

Examples of the "13-oxo fatty acid" produced by the above-mentioned production method 5 include 13-oxo-cis-9-octadecenoic acid induced from cis-9,cis-12-octadecadienoic acid (linoleic acid), 13-oxo-cis-6,cis-9-octadecadienoic acid induced from cis-6,cis-9,cis-12-octadecatrienoic acid (γ-linolenic acid), 13-oxo-cis-9,cis-15-octadecadienoic acid induced from cis-9,cis-12,cis-15-octadecatrienoic acid (α-linolenic acid), 13-oxo-cis-6,cis-9,cis-15-octadecatrienoic acid induced from cis-6,cis-9,cis-12,cis-15-octadecatetraenoic acid (stearidonic acid), 10,13-dioxo-octadecanoic acid induced from 10-hydroxy-cis-12-octadecenoic acid or 10-oxo-cis-12-octadecenoic acid, 10,13-dioxo-cis-6-octadecenoic acid induced from 10-hydroxy-cis-6,cis-12-octadecadienoic acid or 10-oxo-cis-6,cis-12-octadecadienoic acid, 10,13-dioxo-cis-15-octadecenoic acid induced from 10-hydroxy-cis-12,cis-15-octadecadienoic acid or 10-oxo-cis-12,cis-15-octadecadienoic acid, 10,13-dioxo-cis-6,cis-15-octadecadienoic acid induced from 10-hydroxy-cis-6,cis-12,cis-15-octadecatrienoic acid or 10-oxo-cis-6,cis-12,cis-15-octadecatrienoic acid, 13-oxo-cis-5,cis-9-octadecadienoic acid induced from cis-5,cis-9,cis-12-octadecatrienoic acid (pinolenic acid), 13-oxo-trans-5,cis-9-octadecadienoic acid induced from trans-5,cis-9,cis-12-octadecatrienoic acid (columbinic acid) and the like.

Examples of the "10-oxo fatty acid" produced by the above-mentioned production method 6 include 10-oxo-hexadecanoic acid induced from cis-9-hexadecenoic acid (pulmitoleic acid) and the like.

Examples of the "15-oxo fatty acid" produced by the above-mentioned production method 7 include 15-oxo-cis-11-eicosenoic acid induced from cis-11,cis-14-eicosadienoic acid, 15-oxo-cis-11,cis-17-eicosadienoic acid induced from cis-11,cis-14,cis-17-eicosatrienoic acid, 15-oxo-cis-8, cis-11-eicosadienoic acid induced from cis-8,cis-11,cis-14-eicosatrienoic acid (dihomo-γ-linolenic acid), 15-oxo-cis-5,cis-8,cis-11-eicosatrienoic acid induced from cis-5,cis-8,cis-11,cis-14-eicosatetraenoic acid (arachidonic acid), 15-oxo-cis-8,cis-11,cis-17-eicosatrienoic acid induced from cis-8,cis-11,cis-14,cis-17-eicosatetraenoic acid, 15-oxo-cis-5,cis-11-eicosadienoic acid induced from cis-5,cis-11,cis-14-eicosatrienoic acid (sciadonic acid), 15-oxo-cis-5,cis-11,cis-17-eicosatrienoic acid induced from cis-5,cis-11,cis-14,cis-17-eicosatetraenoic acid (juniperonic acid) and the like.

Examples of the "12-oxo fatty acid" produced by the above-mentioned production method 8 include 12-oxo-octadecanoic acid induced from cis-11-octadecenoic acid (cis-vaccenic acid), 12-oxo-cis-14-eicosenoic acid induced from cis-11,cis-14-eicosadienoic acid, 12-oxo-cis-14,cis-17-eicosadienoic acid induced from cis-11,cis-14,cis-17-eicosatrienoic acid, 12-oxo-cis-8,cis-14-eicosadienoic acid induced from cis-8,cis-11,cis-14-eicosatrienoic acid (dihomo-γ-linolenic acid), 12-oxo-cis-5,cis-8-eicosadienoic acid induced from cis-5,cis-8,cis-11-eicosatrienoic acid (mead acid), 12-oxo-cis-8,cis-14,cis-17-eicosatrienoic acid induced from cis-8,cis-11,cis-14,cis-17-eicosatetraenoic acid, 12-oxo-cis-5,cis-8,cis-14-eicosatrienoic acid induced from cis-5,cis-8,cis-11,cis-14-eicosatetraenoic acid (arachidonic acid) and the like.

The dehydrogenase to be used in the above-mentioned production methods 5-8, production method B or production method II is not particularly limited as long as it is an enzyme capable of converting 13-hydroxy fatty acid, 10-hydroxy fatty acid, 15-hydroxy fatty acid, 12-hydroxy fatty acid, 14-hydroxy-cis-4,cis-7,cis-10,cis-16,cis-19-docosapentaenoic acid, 10-hydroxy-tetradecanoic acid utilized as substrates to 13-oxo fatty acid, 10-oxo fatty acid, 15-oxo fatty acid, 12-oxo fatty acid, 14-oxo-cis-4,cis-7,cis-10,cis-16,cis-19-docosapentaenoic acid, 10-oxo-tetradecanoic acid, respectively and, for example, *lactobacillus*-derived hydroxylated fatty acid-dehydrogenase (CLA-DH) is preferable. More preferred is *Lactobacillus plantarum*-derived CLA-DH, and particularly preferred is *L. plantarum* FERM BP-10549 strain-derived CLA-DH. CLA-DH can be obtained by the method described in JP-A-2007-259712, the method described in WO 2013/168310. Dehydrogenase may be a purified one or a crudely purified one. Alternatively, dehydrogenase may be expressed in fungus such as *Escherichia coli* and the like and the fungus itself may be used or culture medium thereof may be used. Furthermore, the enzyme may be of a free form, or immobilized by various carriers.

The dehydrogenation reaction is performed in a suitable buffer (e.g., phosphate buffer, tris buffer, borate buffer etc.) by mixing 13-hydroxy fatty acid, 10-hydroxy fatty acid, 15-hydroxy fatty acid, 12-hydroxy fatty acid, as substrates and dehydrogenase at suitable concentrations and incubating the mixture. The substrate concentration is, for example, 0.01-100 g/L, preferably 0.05-50 g/L, more preferably 0.1-5 g/L. The amount of dehydrogenase to be added is, for example, 0.001-10 mg/mL, preferably 0.005-1 mg/mL, more preferably 0.05-0.2 mg/mL.

A "cofactor" may be used for the dehydrogenation reaction and, for example, $NAD^+$, $NADP^+$ and the like can be used. The concentration of addition thereof may be any as long as the hydration reaction proceeds efficiently. It is preferably 0.001-20 mM, more preferably 0.01-10 mM.

The dehydrogenation reaction is desirably performed within the ranges of preferable temperature and preferable pH of dehydrogenase. For example, the reaction temperature is 5-50° C., preferably 20-45° C. The pH of the reaction mixture is, for example, pH 4-10, preferably pH 5-9. The reaction time is not particularly limited and it is, for example, 10 min-72 hr, preferably 30 min-36 hr.

In one embodiment of the present invention, dehydrogenase is subjected to the reaction system in the form of recombinant cells (e.g., *Escherichia coli, Bacillus subtilis*, yeast, insect cell, animal cell etc.) introduced with an expression vector containing a nucleic acid encoding same. In this case, the oxidation reaction can also be performed by cultivating the cells in a liquid medium suitable for the culture of the cells and added with a substrate and, where necessary, a cofactor and an activator.

In addition, by replacing the dehydrogenation reaction with a chemical oxidation using chromic acid, an oxo fatty acid similar to that by enzyme reaction can be chemically obtained.

As the chemical oxidation, methods known per se, for example, chromic acid oxidation, preferably Jones oxidation and the like can be mentioned. As the chromic acid, salts or complexes of the compound such as anhydrous chromic acid $CrO_3$, chromic acid $H_2CrO_4$ and dichromic acid $H_2Cr_2O_7$ can be used.

To be specific, sulfuric acid (2.3 ml) and water (7.7 ml) are added to anhydrous chromic acid (2.67 g), and acetone (90 ml) is added to the mixture to give a chromic acid solution. 2 g of hydroxylated fatty acid and 40 ml of acetone are added in an Erlenmeyer flask, and the above-mentioned chromic acid solution is added by one drop while stirring in a stirrer on ice. When the solution turns from blue to tea green, dropwise addition of the chromic acid solution is stopped, and the reaction is discontinued with isopropyl alcohol. The precipitated sediment is filtered through filter paper, placed in a separating funnel, diethyl ether (150 ml) and Milli-Q water (300 ml) are added, the mixture is shaken well, and the diethyl ether layer is washed several times with Milli-Q water. To the diethyl ether layer after washing is added an appropriate amount of sodium sulfate (anhydrous), the mixture is stirred and the residual water is removed. The anhydrous sodium sulfate added is filtered off through filter paper, the obtained diethyl ether layer is concentrated by a rotary evaporator, and the reaction product (oxo fatty acid) and unreacted substrate are extracted.

An extract obtained by an oxidation reaction with anhydrous chromic acid (mixture containing substrate and resultant product (oxo fatty acid)) is subjected to moderate-pressure chromatography, a solution that comes out from the column is recovered in fractions. The recovered each fraction is analyzed by LC/MS and gas chromatography, fractions containing oxo fatty acid alone are collected and concentrated by a rotary evaporator. A part of the obtained final resultant product is methylesterified, the purity of oxo fatty acid is evaluated by gas chromatography, and oxo fatty acid having a purity of not less than 98% can be obtained.

An anti-inflammatory agent containing the rare fatty acid derivative of the present invention can be applied to the prophylaxis or improvement of inflammatory diseases. The "inflammatory disease" is not limited as long as it accompanies an inflammation reaction in vivo, and an "inflammatory disease involving macrophage" is preferable. Examples of the "inflammatory disease" include gout, arteriosclerosis, gastric ulcer, nephritis (glomerulonephritis, IgA nephropathy, diabetic nephropathy etc.), periodontal disease (gingiva inflammation, pericoronitis etc.), hepatitis (alcoholic hepatitis, non-alcoholic hepatitis etc.), cirrhosis, asthma, bronchitis, cerebral infarction, aneurysm, delayed allergy, endometriosis, acute respiratory distress syndrome, disorder due to kidney transplantation, acute myocardial infarction, diabetes, systemic lupus erythematosus, Crohn's disease, atopic dermatitis, pneumonia, arthritis (chronic rheumatoid-like arthritis etc.), endotoxin shock, sepsis due to infections, chronic ulcerative colitis, chronic bronchitis, cystitis, chronic osteomyelitis, erosive esophagitis, cholangitis, chronic cholecystitis, gastritis, chronic cervix inflammation, the following nerve inflammation disease, cancer caused by inflammation and the like. Of these, the "inflammatory disease involving macrophage" includes, for example, hepatitis, asthma, systemic lupus erythematosus, Crohn's disease, atopic dermatitis, arthritis, diabetic neuropathy, and dementia.

Furthermore, an anti-inflammatory agent containing the rare fatty acid derivative of the present invention can also be applied to the prophylaxis or improvement of nerve inflammation diseases. The "nerve inflammation disease" refers to a disease caused by nerval inflammation, and the agent can also be used for the prophylaxis or improvement of diabetic neuropathy, dementia (Alzheimer-type etc.), multiple sclerosis and the like. Alternatively, an anti-inflammatory agent containing the rare fatty acid derivative of the present invention can also be applied to the prophylaxis or improvement of cancer caused by inflammation. The "cancer caused by inflammation" is a cancer resulting from chronic inflammation, and the agent can also be used for the prophylaxis or improvement of, for example, large intestine cancer, lung cancer, bladder cancer, mouth cavity cancer, tongue cancer, skin cancer, esophageal cancer, melanoma, bile duct cancer, large intestine cancer, gall bladder cancer, stomach cancer, cervix cancer, liver cancer and the like.

In addition, the rare fatty acid derivative of the present invention can also be used as an inhibitor of M1 macrophage. Activated macrophage becomes M1 macrophage, produces inflammatory mediators such as nitric oxide (NO), prostaglandin E2, TNF-α and the like, and causes chronic inflammations. As shown in the below-mentioned Examples, the rare fatty acid derivative of the present invention has an effect to suppress NO production amount by M1 macrophage, and induce differentiation of macrophage and monocyte, which is a progenitor cell thereof, into M2 macrophage. Differentiation into M2 macrophage can also be induced by a direct action on monocyte or macrophage before differentiation, as well as by an indirect action obtained by placing the intestine in a Th2 cytokine-dominant environment. Therefore, inflammatory diseases involving macrophage can be prevented or improved by suppression of NO production by M1 macrophage, and suppression of differentiation into M1 macrophage by promoting differentiation of macrophage and monocyte into M2 macrophage.

Furthermore, the rare fatty acid derivative of the present invention can also be used as an inhibitor of cell death based on the oxidative stress. The oxidative stress is a stress caused by active oxygen, and examples of the active oxygen include $H_2O_2$, superoxide, hydroxy radical, oxygen and the like. The active oxygen promotes production of inflammatory cytokines and causes inflammatory diseases. Therefore, the inflammatory diseases can be prevented or improved by reducing the oxidative stress.

Alternatively, the rare fatty acid derivative of the present invention can also be used as a promoter of HO-1 expression. HO-1 is an important enzyme as a defense mechanism in the body that protects cells from oxidative stress. Lack of HO-1 promotes cell injury due to oxidative stress and promotes inflammation. Therefore, inflammatory diseases can be prevented or improved by promoting HO-1 expression.

In addition, the rare fatty acid derivative of the present invention can also be used as a promoter of intranuclear expression of Nrf2. When intranuclear expression of Nrf2 is promoted, Nrf2 controls oxidative stress-adoptive reaction and suppresses inflammation. Therefore, inflammatory diseases can be prevented or improved by promoting intranuclear expression of Nrf2.

An anti-inflammatory agent (or M1 macrophage inhibitor, inhibitor of cell death based on oxidative stress, HO-1 expression promoter or Nrf2 intranuclear expression promoter) containing the rare fatty acid derivative of the present invention can be used as, for example, a pharmaceutical product, a food, a feed, a cosmetic and the like, or by adding the agent to them.

The dosage form of the pharmaceutical product includes dispersion, granule, pill, soft capsule, hard capsules, tablet, chewable tablet, quick-integrating tablet, syrup, liquid, suspension, suppository, ointment, cream, gel, adhesive, inhalant, injection and the like. A preparation thereof is prepared according to a conventional method. Since rare fatty acid derivatives are poorly soluble in water, they are dissolved in a non-hydrophilic organic solvent such as plant-derived oil, animal-derived oil and the like or dispersed or emulsified in an aqueous solution together with an emulsifier, a dispersing agent, a surfactant and the like by a homogenizer (high-pressure homogenizer) and used.

Examples of the additives that can be used for formulating include animal and plant oils such as soybean oil, safflower oil, olive oil, germ oil, sunflower oil, beef fat, sardine oil and the like, polyalcohols such as polyethylene glycol, propylene glycol, glycerol, sorbitol and the like, surfactants such as sorbitan ester of fatty acid, sucrose ester of fatty acid, glycerin fatty acid ester, polyglycerol ester of fatty acid and the like, excipients such as purified water, lactose, starch, crystalline cellulose, D-mannitol, lecithin, gum arabic, sorbitol solution, carbohydrate solution and the like, sweetener, colorant, pH adjuster, flavor and the like. A liquid preparation may be dissolved or suspended in water or other suitable medium when in use. Also, tablet and granules may be coated by a well-known method.

For administration in the form of an injection, intravenous, intraperitoneal, intramuscular, subcutaneous, transdermal, intraarticular, intrasynovial, intrathecal, intraperiosteum, sublingual, oral administrations and the like are preferable, and intravenous administration or intraperitoneal administration is particularly preferable. The intravenous administration may be any of drip administration and bolus administration.

When the anti-inflammatory agent of the present invention is used as a food or a food additive, the form of the food is not particularly limited as long as it permits oral ingestion, such as solution, suspension, powder, solid formed article and the like. Specific examples include supplements (powder, granule, soft capsule, hard capsule, tablet, chewable tablet, quick-integrating tablet, syrup, liquid etc.), drinks (carbonic acid drinks, lactic acid drinks, sport drinks, fruit juice drinks, vegetable drinks, soymilk beverage, coffee drinks, tea drinks, powder drinks, concentrated drinks, nutrition drinks, alcohol drinks etc.), confectionery (gummy candy, jelly, gum, chocolate, cookie, candy, caramel, Japanese confectionery, snack etc.), instant food (instant noodles, retort food, can, microwavable foods, instant soup, miso soups, freeze-dried food etc.), oil, fats and oils food (mayonnaise, dressing, butter, cream, margarine etc.), wheat powder products (bread, pasta, noodle, cake mix, bread crumb etc.), seasoning (sauce, tomato processing seasoning, flavor seasoning, cooking mixture, soup etc.), processed meat products (meat ham, sausage etc.).

The above-mentioned foods can contain, where necessary, various nutrients, various vitamins (vitamin A, vitamin B1, vitamin B2, vitamin B6, vitamin C, vitamin D, vitamin E, vitamin K etc.), various minerals (magnesium, zinc, iron, sodium, potassium, selenium etc.), dietary fiber, dispersing agent, stabilizer such as emulsifier and the like, sweetener, flavor components (citric acid, malic acid etc.), flavor, royal jelly, propolis, *Agaricus* and the like.

When the anti-inflammatory agent of the present invention is used as a feed or a feed additive, the feed is, for example, pet food, stock raising or aquaculture feed additive and the like.

When the anti-inflammatory agent of the present invention is used as a cosmetic or a cosmetic additive, the cosmetic is, for example, cream, gel, skin milk, serum, toner, microemulsion essence, facial mask, foundation, lip rouge, eye shadow, shampoo, conditioner, bath additive and the like, and a flavor and the like may be mixed therewith.

Only one kind of rare fatty acid derivative may be blended with the pharmaceutical product, food, feed, cosmetic and the like of the present invention or two or more kinds thereof may be used in combination.

The dose of the pharmaceutical product of the present invention or the ingestion amount of the food of the present invention can be appropriately determined according to the age and body weight of the patients or those who ingest same, symptom, administration time, dosage form, administration method, combination of medicaments and the like. For example, when the pharmaceutical product of the present invention is orally administered, the total amount of the rare fatty acid derivative as an active ingredient is 0.02-100 mg/kg body weight, preferably 0.2-50 mg/kg body weight, per day for an adult, or 0.002 mg-50 mg/kg body weight, preferably 0.02-50 mg/kg body weight, by parenteral administration, which can be administered once a day or in several (2-5) portions per day. When it is ingested as a food, it can be added to a food such that the total ingestion amount of the rare fatty acid derivative as an active ingredient is 1-6000 mg, preferably 10-3000 mg, per day for an adult. The ingestion amount of the feed of the present invention and the amount of use of the cosmetic of the present invention can each appropriately determined according to the above-mentioned ingestion amount of the food and the above-mentioned dose of the pharmaceutical product.

The present invention is explained in more detail in the following by referring to Examples. The Examples are mere exemplifications of the present invention and do not limit the scope of the present invention in any manner.

EXAMPLES

The following rare fatty acid derivatives (No. 4-No. 23) used in the present invention were prepared based on the above-mentioned methods, and other fatty acids (No. 1-No. 3, No. 24, LA, ALA, GLA) were purchased as general reagents. BAY11-7082, which is a IκBα phosphorylation inhibitor, was purchased from Cayman Chemical, and other reagents were purchased from Wako Pure Chemical Industries, Ltd. or Nacalai Tesque and others.

No. 1: trans-10,cis-12-octadecadienoic acid
No. 2: cis-9,trans-11-octadecadienoic acid
No. 3: trans-9,trans-11-octadecadienoic acid
No. 4: 10-hydroxy-cis-12-octadecenoic acid
No. 5: 10-hydroxy-octadecanoic acid
No. 6: 10-oxo-cis-12-octadecenoic acid
No. 7: 10-hydroxy-cis-12,cis-15-octadecadienoic acid
No. 8: 10-oxo-cis-12,cis-15-octadecadienoic acid
No. 9: 10-oxo-cis-6,cis-12-octadecadienoic acid
No. 10: 12-hydroxy-octadecanoic acid
No. 11: 10-oxo-trans-11-octadecenoic acid
No. 12: 10-oxo-trans-11,cis-15-octadecadienoic acid
No. 13: 10-oxo-cis-6,trans-11-octadecadienoic acid
No. 14: 13-hydroxy-cis-9-octadecenoic acid
No. 15: 13-oxo-cis-9-octadecenoic acid
No. 16: 13-oxo-cis-9,cis-15-octadecadienoic acid
No. 17: 13-oxo-cis-6,cis-9-octadecadienoic acid
No. 18: 10,13-dihydroxy-octadecanoic acid
No. 19: 13-hydroxy-cis-6,cis-9-octadecadienoic acid
No. 20: 10,13-dihydroxy-cis-6-octadecenoic acid
No. 21: 10-hydroxy-cis-6,cis-12-octadecadienoic acid
No. 22: 13-hydroxy-cis-9,cis-15-octadecadienoic acid
No. 23: 10,13-dihydroxy-cis-15-octadecenoic acid
No. 24: trans-9,trans-11,trans-13-octadecatrienoic acid
LA: linoleic acid
GLA: γ-linolenic acid
ALA: α-linolenic acid
tBHQ: tert-butylhydroquinone

Example 1 (Evaluation of NO Production Amount by Griess Method)

Figure 1:
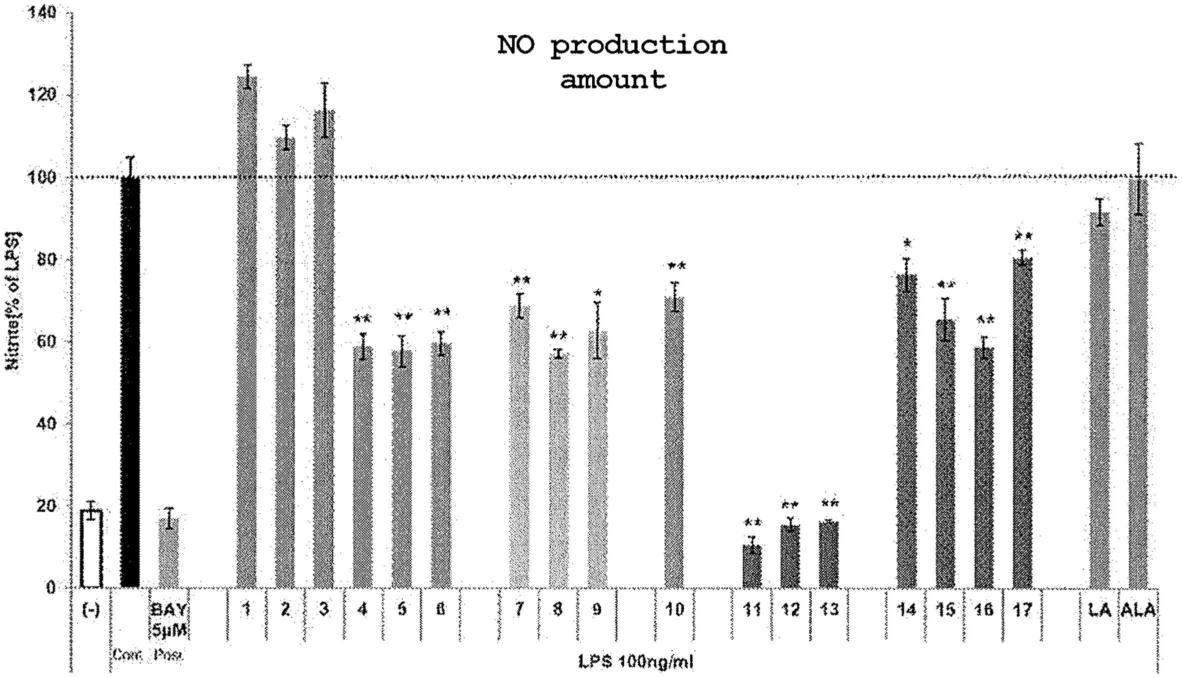
FIG. 1 shows the measurement results of NO production amount by the Griess method, wherein Cont. shows negative control (ethanol addition), Posi. shows positive control (IκBα phosphorylation inhibitor addition), and the vertical axis shows NO production amount.

The mouse-derived macrophage-like cell line RAW264.7 was seeded in a 48 well plate $1\times10^5$ cells per well. After culture for 5 hr, *Escherichia coli*-derived lipopolysaccharide (LPS) was added to 100 ng/mL over 24 hr to activate RAW264.7 cells. Simultaneously with LPS, various compounds (No. 1-No. 17, LA, ALA) were added at 10 μM, and the concentration of nitrous acid ($NO_2^-$), which is an oxide of nitric oxide (NO) produced by macrophage activation, in the culture medium was measured. The amount of $NO_2$ in the culture medium was quantified by the Griess method and in reference to Shan Lin et al., Molecular Nutrition and Food Research 57 (2013) p 1135-1144, "Auraptene suppresses inflammatory responses in activated RAW264 macrophages by inhibiting p38 mitogen-activated protein kinase activation", the section of Material and methods Measurements of TNF-α, MCP-1, and NO concentrations. The quantification was actually performed as follows. RAW264.7 culture medium treated with LPS and various compounds for 24 hr was recovered. 0.2% N-(1-naphthyl) ethylenediamine and 2% Sulfanilamide/10% $H_3PO_4$ were blended at 1:1 immediately before reaction to give a Griess reagent, RAW264.7 culture medium and the Griess reagent were mixed at 1:1 and reacted at room temperature for 10 min. After completion of the reaction, absorbance at 550 nm was measured. $NaNO_2$ was used as the $NO_2^-$ standard product, and the $NO_2^-$ concentration in the culture medium was calculated. The concentration of the sample was adjusted with ethanol. Ethanol was used as a negative control, and BAY11-7082 (5 μM), which is a IκBα phosphorylation inhibitor, was used as a positive control. The results are shown in FIG. 1.

Example 2 (Evaluation of Anti-Stress Activity to $H_2O_2$)

Figure 2:
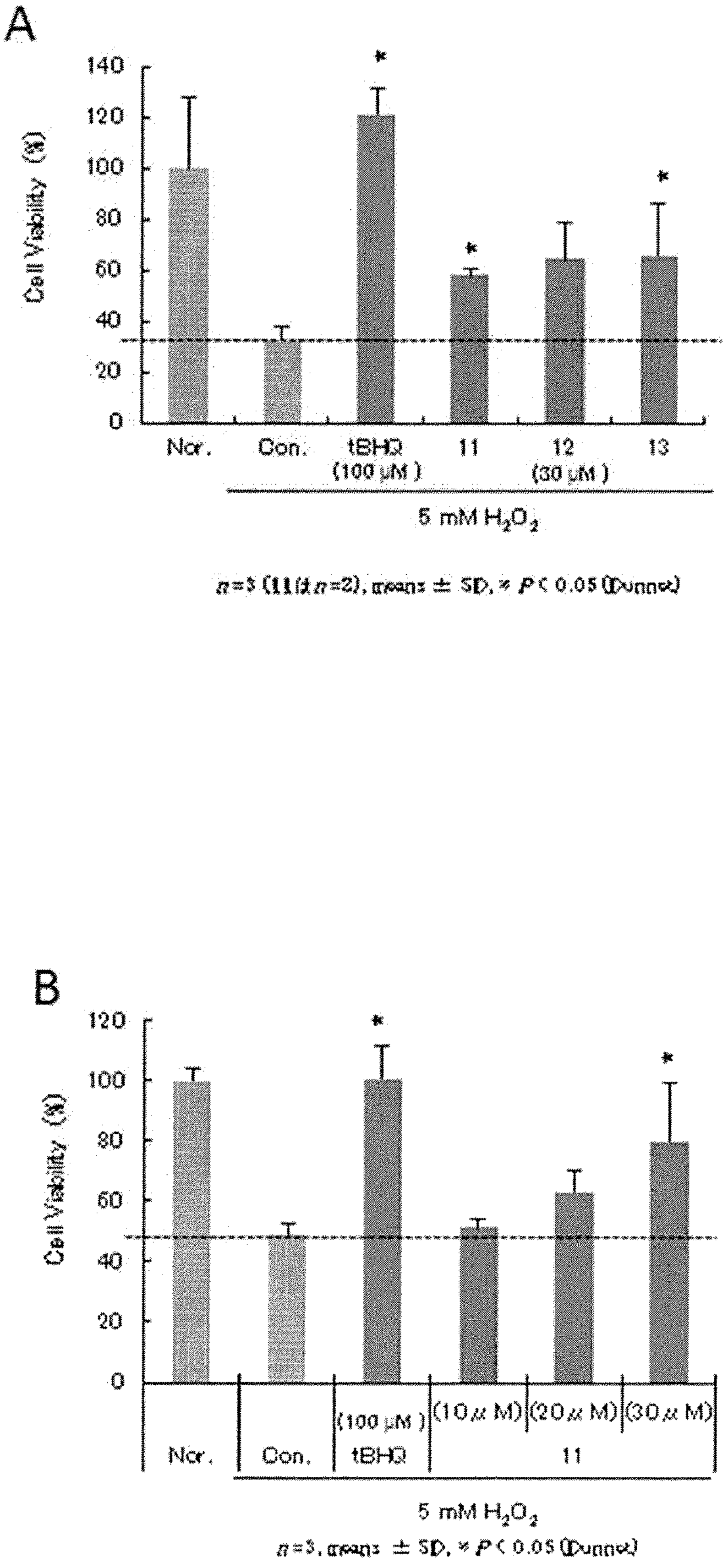
FIG. 2 shows the measurement results of cell survival rate relative to $H_2O_2$. A: Various compounds (No. 11-No. 13)

The cell line HepG2 derived from human liver cancer was cultured in D-MEM (10% FBS, 100 U/mL penicillin, 100 μg/mL streptomycin), seeded in a 96 well plate at $3.0\times10^4$ cells/well, and cultured at 37° C., 5% $CO_2$ for 24 hr. Various compounds (tBHQ, No. 11-No. 13) were dissolved in serum-free D-MEM (100 U/mL penicillin, 100 μg/mL streptomycin, 0.1% BSA, 0.3% ethanol) to prepare test media having adjusted concentrations. The supernatant was removed from the 96 well plate, the above-mentioned test medium was added at 100 μL/well, and the cells were cultured at 37° C., 5% $CO_2$ for 24 hr. Thereafter, the supernatant was removed again from the 96 well plate, 5 mM $H_2O_2$-containing D-MEM (100 U/mL penicillin, 100 μg/mL streptomycin) was added at 100 μL/well, 37° C., and the cells were cultured at 5% $CO_2$ for 30 min. The supernatant was removed from the 96 well plate, WST-1 reagent-containing D-MEM (7 μg/mL 1-Methosy PMS, 33 μg/mL WST-1) was added at 100 μL/well, the cells were cultured at 37° C., 5% $CO_2$ for 2 hr, and the absorbance at 450 nm was measured. The results are shown in FIG. 2A, B.

Example 3 (Effect on Anti-Oxidant Enzyme HO-1 mRNA Expression)

HepG2 cells were seeded in a 24 well plate at $1.5\times10^5$ cells/well, and cultured at 37° C., 5% $CO_2$ for 24 hr. Various compounds (tBHQ, No. 11-No. 13) were dissolved in serum-free D-MEM (100 U/mL penicillin, 100 μg/mL streptomycin, 0.1% BSA, 0.3% ethanol) to prepare test media having adjusted concentrations. The supernatant was removed from the 24 well plate, the above-mentioned test medium was added at 500 μL/well, and the cells were cultured at 37° C., 5% $CO_2$ for 6 hr. Thereafter, the supernatant was removed again from the 24 well plate, the cells were washed twice with sterile PBS, and the cells were recovered using 300 μL/well Sepasol. RNA was extracted from the recovered cells, and cDNA was synthesized. Real-time PCR method was performed using the cDNA as a template, and SYBR Green, and the expression of anti-oxidant enzyme HO-1 mRNA was evaluated. GAPDH was used as the internal standard, and 43 cycles of initial denaturation at 95° C. for 15 min, amplification reaction at 95° C. for 15 sec and 60° C. for 30 sec were performed under PCR conditions. The results are shown in FIG. 3A, B.

Example 4 (Effect on Intranuclear Expression of Transcription Factor Nrf2 Involved in Anti-Oxidation Reaction)

HepG2 cells were seeded in a 12 well plate at $3.0\times10^4$ cells/well, and cultured at 37° C., 5% $CO_2$ for 24 hr. Various compounds (tBHQ, No. 11-No. 13) were dissolved in serum-free D-MEM (100 U/mL penicillin, 100 μg/mL streptomycin, 0.1% BSA, 0.3% ethanol) to prepare test media having adjusted concentrations. The supernatant was removed from the 12 well plate, the above-mentioned test medium was added at 1 mL/well, and the cells were cultured at 37° C., 5% $CO_2$ for 24 hr. Thereafter, the supernatant was removed again from the 12 well plate, the cells were washed with sterile PBS, and dissolved in 100 μL of dissolution buffer (10 mM HEPES-KOH, 250 mM sucrose, 10 mM potassium chloride, 1.5 mM magnesium chloride, 1 mM EDTA, 1 mM EGTA, proteinase inhibitor cocktail, pH 7.6). The solution was centrifuged at 1,000×g, 4° C. for 5 min, the supernatant was removed, cell pellets were dissolved in 30 μL of nucleus extraction buffer (20 mM HEPES-KOH, 100 mM sodium chloride, 1% SDS, 1 mM EDTA, 1 mM EGTA, proteinase inhibitor cocktail, pH 6.8), and the mixture was shaken at 4° C. for 1 hr. Thereafter, the solution was centrifuged at 10,000×g, 4° C. for 15 min, the supernatant was recovered to give a nucleoprotein fraction. The above-mentioned supernatant recovered as the nucleoprotein fraction was measured for the protein concentration by using Bio-Rad DC Protein Assay kit, diluted to the same protein amount and used as a sample. To the above-mentioned sample were added a loading buffer and 2-mercaptoethanol and the mixture was boiled at 95° C. for 5 min. The above-mentioned boiled sample was applied by 20 μL each to 5% concentration gel and 10% electrophoresis gel, and the mixture was electrophoresed at 20 mA for 20 min and 150 V for 60 min. The protein was transferred from the gel on a PVDF membrane at 15 V for 35 min, the PVDF membrane after transfer was immersed in a blocking buffer, and stood overnight. Then, the PVDF membrane was reacted with a 400-fold diluted anti-human Nrf2 rabbit antibody for 2 hr, washed and reacted with 500-fold diluted HRP-labeled anti-rabbit IgG for 1 hr. Using Chemi-Lumi One Super, the band on the PVDF membrane was detected. The results are shown in FIG. 4.

Example 5 (Effect on Transcription Activity of Transcription Factor Nrf2 Involved in Anti-Oxidation Reaction)

Rat adrenal gland medulla pheochromocytoma PC12 cells incorporating a luciferase gene expression vector containing a luciferase gene linked to a rat NQO1 promoter region containing the binding region of rat Nrf2 were cultured in D-MEM (High-Glucose, 15% HS, 5% FBS, 300 mg/mL hygromycin B). The cells were seeded in a 96 well plate at PC12 cells $5.0\times10^4$ cells/well, and cultured at 37° C., 5% $CO_2$ for 24 hr. Various compounds (tBHQ, No. 11-No. 13) were dissolved in D-MEM (High-Glucose, 15% HS, 5% FBS, 300 mg/mL hygromycin B, 0.3% ethanol) to prepare test media having adjusted concentrations. The supernatant was removed from the 96 well plate, the above-mentioned test medium was added at 100 μL/well, and the cells were cultured at 37° C., 5% $CO_2$ for 9 hr. Thereafter, the supernatant was removed again from the 96 well plate, luminescence reagent was added at 50 μL/well, and the luminescence intensity was measured. The results are shown in FIG. 5.

Example 6 (Effect to Differentiate Macrophage into M2 Macrophage)

C57BL/6N mouse (male, 6- to 12-week-old) (SHIMIZU experiment material) was sacrificed by cervical dislocation, and femur including the knee joint and the hip joint was isolated. The femur was transferred to a 100 mm dish (Thermo Fisher Scientific) containing RPMI 1640 medium (nacalai tesque), and the bone marrow fluid was collected on the dish from the femur. The cell aggregates in the dish were suspended, and placed in a 50 mL centrifugation tube. The suspended cell aggregates were centrifuged at 1500 rpm for 10 min, the supernatant was removed, the cell pellets were suspended in 2 mL of RBC lysis buffer (0.01 M Tris-HCl buffer containing 8.3 g/L ammonium chloride), and the suspension was stood for 3 min. Thereafter, the medium (8 mL) was added to quench the reaction by dilution, the mixture was centrifuged at 1500 rpm for 10 min, and the supernatant was removed. A single cell suspension of bone marrow-derived cells was prepared from the cell pellets by using a 40 μm-cell strainer (BD Bioscience).

The viable cells in the above-mentioned bone marrow-derived cells were counted by using Trypan Blue staining solution (nacalai tesque), seeded in a 100 mm dish at a density of $1.2\times10^6$ cells/dish, and cultured in a $CO_2$ incubator according to the schedule described in FIG. 6. As a cell medium, RPMI 1640 medium added with 10% FBS (Biowest), 1% Penicillin/Streptomycin (nacalai tesque), 20% (v/v) L929 conditioned medium and 55 μM β-mercaptoethanol (Gibco) was used. On day 6 of culture, IL-4 (20 ng/mL) and various compounds (LA, GLA, ALA, No. 1-3, 7, 8, 9, 14-24) (30 μM) were added to the medium.

(1) Cell Surface Antigen Expressing on M2 Macrophage

The cell surface antigen expressing on M2 macrophage at 48 hr after addition of IL-4 and various compounds (LA, GLA, ALA, No. 1-3, 7, 8, 9, 14-24) was confirmed. First, the cells were recovered in a 4 mL Falcon tube (BD Bioscience), and centrifuged at 1500 rpm for 5 min to give cell pellets. The cells were washed with FACS buffer (0.1% BSA (fatty acid free) (nacalai tesque), and the cell pellets were uniformized by tapping. Furthermore, BD Pharmingen™ Purified Rat anti-Mouse CD16/CD32 (BD Bioscience) was added, and the mixture was tapped and stood at 4° C. for 10 min (Fc blocking). To detect the cell surface antigen (CD206, F4/80) expressing on M2 macrophage, a fluorochrome-labeled monoclonal antibody (Anti-Mouse CD206 Alexa Fluor 647 (BioLegend), Anti-Mouse F4/80 Antigen FITC (eBioscience)) was added, and the mixture was tapped and stood at 4° C. for 30 min. Thereafter, the cells were washed with FACS buffer, the cell pellets were uniformized by tapping, and Viability Dye 7-AAD (eBioscience) was added. The cell surface antigen was measured by BD Accuri™ C6 flow cytometer (BD Bioscience). For the analysis, FlowJo™ (Tomy Digital Biology) was used. The results are shown in FIGS. 7-10.

(2) mRNA Expression of M2 Macrophage

At 24 hr after addition of IL-4 and various compounds (ALA, No. 7, 8, 16, 22, 23), mRNA (Arginase 1, IL-1β) expression of the cells was confirmed. First, cells were seeded in a well, 700 μL of Sepasol RNAIsuper (nacalai tesque) was added and the mixture was shaken for 30 min. The cells were dispersed and the dispersion was transferred into a 1.5 mL tube. To the 1.5 mL tube was added 150 μL of chloroform (nacalai tesque), mixed by inverting, stood at room temperature for 5 min, and centrifuged at 4° C., 15,000 rpm for 65 min. The aqueous layer (350 μL) was transferred into another 1.5 mL tube, 350 μL of isopropanol (nacalai tesque) were further added. The tube was mixed by inverting, stood at room temperature for 15 min, and centrifuged at 4° C., 15,000 rpm for 65 min, and the supernatant was removed. To the precipitate was added 500 μL of 75% ethanol (nacalai tesque) and the mixture was centrifuged at 4° C., 15,000 rpm for 15 min, and the upper layer was removed. This operation was performed twice in total. The obtained precipitate (Total RNA) was air dried for about 40 min, dissolved in 20 μL of Ultra pure water (Invitrogen), and the mRNA concentration was measured by Nano Drop (Scrum). The mRNA concentration was adjusted with Ultra pure water to 1000 ng/μL on ice to give an RNA solution. Oligo dT primer (Gibco) (1 μL) and RNA solution (10 μL) (1000 ng/μL) were added into a 0.2 mL 8-tube, incubated in a Thermal Cycler at 70° C. for 10 min to destroy the higher order structure of RNA. Furthermore, the reagents shown in Table 1 were added to the 0.2 mL 8-tube, and the mixture was incubated in a Thermal Cycler (TAKARA) at 42° C. for 50 min and at 70° C. for 15 min. After cooling on ice, the reaction mixture was gathered on the bottom of the tube by light centrifugation, and cDNA was obtained.

TABLE 1

| | |
|---|---|
| RNA sample/primer mixture | 10 μl |
| 5× reverse transcription buffer (Promega) | 4 μl |
| RNase inhibiter (TOYOBO) | 0.5 μl |
| 2.5 mM dNTP Mix (TAKARA) | 2 μl |
| Nuclease Free Water | 2.5 μl |
| Superscript (II) reverse transcriptase (Promega) | 1 μl |
| Total | 20 μl |

The obtained cDNA was diluted 5-fold with Ultra pure water. A plasmid solution (5 μL) to be used as the standard was taken in a 0.6 mL tube, and diluted 10-fold with Ultra pure water (45 μL). This operation was repeated, and a plasmid solution diluted $10^2$- to $10^9$-fold was produced. The reagent shown in Table 2 per sample was prepared in a 1.5 mL tube and dispensed to a 96 well plate by 12 μL each. Ultra pure water as a negative control, the dilution solution ($10^3$-$10^8$ dilution) at each concentration produced above as the standard, and cDNA of a sample for measurement were added by 3 μL each to the plate. The plate was set in Light-Cycler™ (Roche), and PCR was performed. With each of the Arginase 1 mRNA expression level and IL-1β expression level of the cells added with IL-4 alone as 1, the Arginase 1 mRNA expression level and IL-1β expression level when IL-4 and various compounds were concurrently added are shown in FIGS. 11, 12.

TABLE 2

| | |
|---|---|
| $dH_2O$ | 8.4 μl |
| SYBR Green (TOYOBO) | 8.0 μl |
| Total | 0.8 μl |

Example 7 (Effect of Differentiation of Monocyte into M2 Macrophage)

It is considered that, in the body, an inflammatory macrophage is released in blood in a monocyte state and, after circulation in the whole body, infiltrates into the peripheral tissues, and differentiates into a tissue-specific macrophage according to the environment of the peripheral tissues. In this Example, whether addition of various compounds of fatty acid derivative in the initial stage of differentiation of monocyte into macrophage promotes induction of differentiation of monocyte into M2 macrophage was studied.

Using the bone marrow-derived cells prepared in Example 6 and considering from the initial day of culture to day 3 of culture as the initial stage of differentiation, culture according to the schedule described in FIG. 13 was performed. As the cell medium, RPMI 1640 medium added with 10% FBS, 1% Penicillin/Streptomycin, 5% (v/v) L929 conditioned medium and 55 μM β-mercaptoethanol (Gibco), IL-4 (20 ng/mL) and various compounds (ALA, No. 7, 8, 16, 22, 23) (30 μM) was used from the initial day of culture to day 3 of culture. After day 3 of culture, RPMI 1640 medium added with 10% FBS, 1% Penicillin/Streptomycin, 20% (v/v) L929 conditioned medium and 55 μM β-mercaptoethanol (Gibco) was used. The cells on day 7 of culture were recovered, and mRNA expression and cell surface antigen were confirmed in the same manner as in Example 6. The results are shown in FIGS. 14-17.

Example 8 (Effect on Intestinal Mucosa Immune System to Differentiate Monocyte into M2 Macrophage)

It is known that various environmental factors such as cytokine and the like in the peripheral tissue are important for the differentiation of monocyte into M2 macrophage. Therefore, whether a Th2 cytokine dominant environment can be formed in the intestine as a result of an interaction between immunocyte and various compounds of fatty acid derivatives was studied.

BALB/c mouse (♂, 6- to 12-week-old) (fresh water experiment material) was sacrificed by cervical dislocation, and the mesenteric lymph node and Peyer's patch were isolated. Each tissue was finely cut, and treated with RPMI 1640 (5% FBS, 1.0 mg/mL Collagenase containing) medium at 37° C. for 30 min. The tissue was further mashed with the plunger part of a 1 mL syringe to give a cell suspension. The cell suspension was centrifuged at 1500 rpm for 10 min, the supernatant was removed and, using a 40 μm-cell strainer, a single cell suspension of the mesentericlymph node-derived cells and a single cell suspension of the Peyer's patch-derived cells were prepared.

In addition, BALB/c mouse was sacrificed by cervical dislocation, and the spleen was isolated. The spleen was mashed on a 100 mm dish to give a cell suspension. The cell aggregates in the dish were suspended, and placed in a 50 mL centrifugation tube. The suspended cell aggregates were centrifuged at 1500 rpm for 10 min, the supernatant was removed, the cell pellets were suspended in 2 mL of RBC lysis buffer, and the suspension was stood for 3 min. Thereafter, the medium (8 mL) was added to quench the reaction by dilution, the mixture was centrifuged at 1500 rpm for 10 min, and the supernatant was removed. A single cell suspension of spleen-derived cells was prepared from the cell pellets by using a 40 μm-cell strainer.

The viable cells in each of the above-mentioned mesentericlymph node-derived cells, Peyer's patch-derived cells and spleen-derived cells were counted by using Trypan Blue staining solution, seeded at $1.0 \times 10^6$ cells/well in a 96 well plate, various compounds (ALA, No. 7, 8, 16, 22, 23) were added and the cells were cultured for 18-24 hr in the presence of lymphocyte activators PMA and Ionomycin. After culture, each supernatant was recovered. As the medium for culture, RPMI 1640 added with 10% FBS, 1% Penicillin/Streptomycin was used.

The concentration of IL-4 and MCP-1 contained in the each recovered supernatant was measured by ELISA. Basically, the recommended protocol of ELISA Ready-SET-Go!® (eBioscience) was adopted. Capture antibody was diluted with a coating buffer, added to a 96 well plate at 50 μL/well, and the plate was sealed and stood overnight at 4° C. The well was washed 3 times with 250 μL/well of Wash buffer, ELISA/ELISPOT Diluent was added to the well at 100 μL/well, and the mixture was stood at room temperature for 1 hr. 50 μL/well of standard and each supernatant were added to the well, the well was stood at room temperature for 2-3 hr and washed 3 times with Wash buffer at 250 μL/well. Detection antibody was diluted with ELISA/ELISPOT Diluent, added to the well at 50 μL/well, the well was stood at room temperature for 1 hr, and washed 3 times with 250 μL/well of Wash buffer. Avidin-HRP was diluted with ELISA/ELISPOT Diluent, was added to the well at 50

μL/well, and the well was stood at room temperature for 15 min and washed 6 times with 250 μL/well of Wash buffer. TMB solution was added to the well at 50 μL/well, and the well was stood at room temperature for 15 min. 1 M $H_3PO_4$ solution was added to the well at 25 μL/well to discontinue the enzyme reaction. The absorbance at wavelength 450 nm was measured by a Microplate Reader. The results are shown in FIGS. 18, 19.

While the present invention has been described with emphasis on preferred embodiments, it is obvious to those skilled in the art that the preferred embodiments can be modified.

The contents disclosed in any publication cited herein, including patents and patent applications, are hereby incorporated in their entireties by reference, to the extent that they have been disclosed herein.

INDUSTRIAL APPLICABILITY

The present invention has clarified that rare fatty acid derivatives have a conventionally-unknown anti-inflammatory effect as a physiological function thereof. An anti-inflammatory agent containing the rare fatty acid derivative is applicable to various fields such as pharmaceutical product, food, feed and the like, and the present invention is industrially extremely useful.

This application is based on patent application Nos. 2014-011866 (filing date: Jan. 24, 2014) and 2014-162982 (filing date: Aug. 8, 2014) filed in Japan, the contents of which are incorporated in full herein.

The invention claimed is:

1. A method for inducing differentiation of macrophage into M2 macrophage, comprising administering to a patient an effective amount of a fatty acid, wherein the fatty acid is 13-hydroxy-cis-9, cis-15-octadecadienoic acid or 13-oxo-cis-6, cis-9-octadecadienoic acid.

2. The method according to claim 1, wherein the fatty acid is 13-hydroxy-cis-9,cis-15-octadecadienoic acid.

3. The method according to claim 1, wherein the fatty acid is 13-oxo-cis-6,cis-9-octadecadienoic acid.

* * * * *

SEQUENCE LISTING

```
<160> NUMBER OF SEQ ID NOS: 2

<210> SEQ ID NO 1
<211> LENGTH: 1773
<212> TYPE: DNA
<213> ORGANISM: Lactobacillus acidophilus
<220> FEATURE:
<221> NAME/KEY: CDS
<222> LOCATION: (1)..(1773)

<400> SEQUENCE: 1

atg cat tat agt agt ggt aat tat gaa gct ttt gta aac gca agt aaa       48
Met His Tyr Ser Ser Gly Asn Tyr Glu Ala Phe Val Asn Ala Ser Lys
1               5                   10                  15

cct aag gat gtc gat cag aag tcc gca tat ctt gtt ggt tca ggt ttg       96
Pro Lys Asp Val Asp Gln Lys Ser Ala Tyr Leu Val Gly Ser Gly Leu
            20                  25                  30

gca tcg ctt gct agt gct gta ttt tta att cgt gat ggt cac atg aag      144
Ala Ser Leu Ala Ser Ala Val Phe Leu Ile Arg Asp Gly His Met Lys
        35                  40                  45

ggt gat aga att cat atc ctt gaa gaa ttg agc ctt cca ggt ggt tca      192
Gly Asp Arg Ile His Ile Leu Glu Glu Leu Ser Leu Pro Gly Gly Ser
    50                  55                  60

atg gat ggg atc tat aat aag caa aaa gaa agc tac atc att cgt ggt      240
Met Asp Gly Ile Tyr Asn Lys Gln Lys Glu Ser Tyr Ile Ile Arg Gly
65                  70                  75                  80

ggt cgt gaa atg gaa gcc cat ttt gaa tgc ttg tgg gac ttg ttt aga      288
Gly Arg Glu Met Glu Ala His Phe Glu Cys Leu Trp Asp Leu Phe Arg
                85                  90                  95

tcg att cca tca gct gaa aat aaa gat gaa tcg gtc ctg gat gaa ttt      336
Ser Ile Pro Ser Ala Glu Asn Lys Asp Glu Ser Val Leu Asp Glu Phe
            100                 105                 110

tac cgt tta aat aga aaa gat cca agt ttc gca aag act cgt gtc att      384
Tyr Arg Leu Asn Arg Lys Asp Pro Ser Phe Ala Lys Thr Arg Val Ile
        115                 120                 125

gtt aac cgc gga cat gaa ctt cca act gac ggt caa tta ctt ctt act      432
Val Asn Arg Gly His Glu Leu Pro Thr Asp Gly Gln Leu Leu Leu Thr
    130                 135                 140

ccc aag gct gtt aaa gaa att att gat ctt tgc tta act cct gaa aaa      480
Pro Lys Ala Val Lys Glu Ile Ile Asp Leu Cys Leu Thr Pro Glu Lys
145                 150                 155                 160

gat tta caa aat aaa aaa att aat gaa gtc ttt agt aaa gaa ttt ttt      528
Asp Leu Gln Asn Lys Lys Ile Asn Glu Val Phe Ser Lys Glu Phe Phe
                165                 170                 175

gaa tca aac ttc tgg ctt tac tgg tca acg atg ttt gcc ttt gag cca      576
```

-continued

```
Glu Ser Asn Phe Trp Leu Tyr Trp Ser Thr Met Phe Ala Phe Glu Pro
            180                 185                 190

tgg gca agt gcg atg gaa atg cgt cgt tac tta atg cgt ttt gtt caa      624
Trp Ala Ser Ala Met Glu Met Arg Arg Tyr Leu Met Arg Phe Val Gln
        195                 200                 205

cac gtt tct aca ctt aag aat tta tca tca cta cgc ttt act aag tat      672
His Val Ser Thr Leu Lys Asn Leu Ser Ser Leu Arg Phe Thr Lys Tyr
    210                 215                 220

aac caa tat gaa tca tta att tta cca atg gtt aaa tac ttg aaa gat      720
Asn Gln Tyr Glu Ser Leu Ile Leu Pro Met Val Lys Tyr Leu Lys Asp
225                 230                 235                 240

cgc ggc gtg caa ttc cat tac aac acc gtt gtt gat aat atc ttt gtt      768
Arg Gly Val Gln Phe His Tyr Asn Thr Val Val Asp Asn Ile Phe Val
                245                 250                 255

aac cgt tca aat ggt gaa aag att gct aag caa att ctt tta act gaa      816
Asn Arg Ser Asn Gly Glu Lys Ile Ala Lys Gln Ile Leu Leu Thr Glu
            260                 265                 270

aac ggt gaa aaa aag agc atc gat tta aca gaa aat gac ctc gtc ttc      864
Asn Gly Glu Lys Lys Ser Ile Asp Leu Thr Glu Asn Asp Leu Val Phe
        275                 280                 285

gtt act aac ggt tca att act gaa agt aca act tat ggt gat aac ttg      912
Val Thr Asn Gly Ser Ile Thr Glu Ser Thr Thr Tyr Gly Asp Asn Leu
    290                 295                 300

cac cca gct tct gag gaa cat aaa tta ggt gct act tgg aaa tta tgg      960
His Pro Ala Ser Glu Glu His Lys Leu Gly Ala Thr Trp Lys Leu Trp
305                 310                 315                 320

caa aac ttg gca gcg caa gat gat gac ttc ggt cac cca gat gtc ttc     1008
Gln Asn Leu Ala Ala Gln Asp Asp Asp Phe Gly His Pro Asp Val Phe
                325                 330                 335

tgc aag gat att cca aag gct aac tgg gta atg tct gct aca att act     1056
Cys Lys Asp Ile Pro Lys Ala Asn Trp Val Met Ser Ala Thr Ile Thr
            340                 345                 350

ttt aag aat aat gat att gtg cca ttc att gaa gca gtt aat aag aag     1104
Phe Lys Asn Asn Asp Ile Val Pro Phe Ile Glu Ala Val Asn Lys Lys
        355                 360                 365

gat cca cac agc ggc tca att gta act agt ggg cct act acg att aag     1152
Asp Pro His Ser Gly Ser Ile Val Thr Ser Gly Pro Thr Thr Ile Lys
    370                 375                 380

gat tct aac tgg cta ctt ggt tat tca atc agt cgt cag cct cac ttt     1200
Asp Ser Asn Trp Leu Leu Gly Tyr Ser Ile Ser Arg Gln Pro His Phe
385                 390                 395                 400

gaa gca caa aag cct aac gaa ttg att gta tgg ctt tat ggt ttg ttc     1248
Glu Ala Gln Lys Pro Asn Glu Leu Ile Val Trp Leu Tyr Gly Leu Phe
                405                 410                 415

tca gac acc aaa ggt aac tat gtt gaa aag act atg cct gac tgt aac     1296
Ser Asp Thr Lys Gly Asn Tyr Val Glu Lys Thr Met Pro Asp Cys Asn
            420                 425                 430

ggt att gaa tta tgt gaa gaa tgg ctt tac cac atg ggt gtt cct gaa     1344
Gly Ile Glu Leu Cys Glu Glu Trp Leu Tyr His Met Gly Val Pro Glu
        435                 440                 445

gaa aga atc cca gaa atg gct tca gct gct acg act att cca gca cac     1392
Glu Arg Ile Pro Glu Met Ala Ser Ala Ala Thr Thr Ile Pro Ala His
    450                 455                 460

atg cca tat att act tca tac ttc atg cca aga gca tta ggc gac aga     1440
Met Pro Tyr Ile Thr Ser Tyr Phe Met Pro Arg Ala Leu Gly Asp Arg
465                 470                 475                 480

ccc aag gtt gtg cca gac cac tca aag aac ttg gcc ttc att ggt aac     1488
Pro Lys Val Val Pro Asp His Ser Lys Asn Leu Ala Phe Ile Gly Asn
                485                 490                 495
```

-continued

```
ttt gct gaa acg cca aga gac act gtc ttt acc act gaa tac tct gtc     1536
Phe Ala Glu Thr Pro Arg Asp Thr Val Phe Thr Thr Glu Tyr Ser Val
            500                 505                 510

aga act gcg atg gaa gct gta tac acc ttg ctt aac att gat cgt ggt     1584
Arg Thr Ala Met Glu Ala Val Tyr Thr Leu Leu Asn Ile Asp Arg Gly
        515                 520                 525

gtg cca gaa gta ttt gca tct gcc ttc gat gtc aga atg ctc atg aac     1632
Val Pro Glu Val Phe Ala Ser Ala Phe Asp Val Arg Met Leu Met Asn
    530                 535                 540

gca atg tac tac ttg aat gat caa aag aag ctt gaa gat ctt gat ttg     1680
Ala Met Tyr Tyr Leu Asn Asp Gln Lys Lys Leu Glu Asp Leu Asp Leu
545                 550                 555                 560

cct att gct gaa aag ttg gca att aag ggg atg ctc aag aaa gtt aag     1728
Pro Ile Ala Glu Lys Leu Ala Ile Lys Gly Met Leu Lys Lys Val Lys
                565                 570                 575

ggc act tat ata gag gaa ttg ctt aag aag tat aag ttg gtt tag         1773
Gly Thr Tyr Ile Glu Glu Leu Leu Lys Lys Tyr Lys Leu Val
            580                 585                 590


<210> SEQ ID NO 2
<211> LENGTH: 590
<212> TYPE: PRT
<213> ORGANISM: Lactobacillus acidophilus

<400> SEQUENCE: 2

Met His Tyr Ser Ser Gly Asn Tyr Glu Ala Phe Val Asn Ala Ser Lys
1               5                   10                  15

Pro Lys Asp Val Asp Gln Lys Ser Ala Tyr Leu Val Gly Ser Gly Leu
            20                  25                  30

Ala Ser Leu Ala Ser Ala Val Phe Leu Ile Arg Asp Gly His Met Lys
        35                  40                  45

Gly Asp Arg Ile His Ile Leu Glu Glu Leu Ser Leu Pro Gly Gly Ser
    50                  55                  60

Met Asp Gly Ile Tyr Asn Lys Gln Lys Glu Ser Tyr Ile Ile Arg Gly
65                  70                  75                  80

Gly Arg Glu Met Glu Ala His Phe Glu Cys Leu Trp Asp Leu Phe Arg
                85                  90                  95

Ser Ile Pro Ser Ala Glu Asn Lys Asp Glu Ser Val Leu Asp Glu Phe
            100                 105                 110

Tyr Arg Leu Asn Arg Lys Asp Pro Ser Phe Ala Lys Thr Arg Val Ile
        115                 120                 125

Val Asn Arg Gly His Glu Leu Pro Thr Asp Gly Gln Leu Leu Leu Thr
    130                 135                 140

Pro Lys Ala Val Lys Glu Ile Ile Asp Leu Cys Leu Thr Pro Glu Lys
145                 150                 155                 160

Asp Leu Gln Asn Lys Lys Ile Asn Glu Val Phe Ser Lys Glu Phe Phe
                165                 170                 175

Glu Ser Asn Phe Trp Leu Tyr Trp Ser Thr Met Phe Ala Phe Glu Pro
            180                 185                 190

Trp Ala Ser Ala Met Glu Met Arg Arg Tyr Leu Met Arg Phe Val Gln
        195                 200                 205

His Val Ser Thr Leu Lys Asn Leu Ser Ser Leu Arg Phe Thr Lys Tyr
    210                 215                 220

Asn Gln Tyr Glu Ser Leu Ile Leu Pro Met Val Lys Tyr Leu Lys Asp
225                 230                 235                 240

Arg Gly Val Gln Phe His Tyr Asn Thr Val Val Asp Asn Ile Phe Val
                245                 250                 255
```

-continued

```
Asn Arg Ser Asn Gly Glu Lys Ile Ala Lys Gln Ile Leu Leu Thr Glu
            260                 265                 270

Asn Gly Glu Lys Lys Ser Ile Asp Leu Thr Glu Asn Asp Leu Val Phe
        275                 280                 285

Val Thr Asn Gly Ser Ile Thr Glu Ser Thr Thr Tyr Gly Asp Asn Leu
    290                 295                 300

His Pro Ala Ser Glu Glu His Lys Leu Gly Ala Thr Trp Lys Leu Trp
305                 310                 315                 320

Gln Asn Leu Ala Ala Gln Asp Asp Asp Phe Gly His Pro Asp Val Phe
                325                 330                 335

Cys Lys Asp Ile Pro Lys Ala Asn Trp Val Met Ser Ala Thr Ile Thr
            340                 345                 350

Phe Lys Asn Asn Asp Ile Val Pro Phe Ile Glu Ala Val Asn Lys Lys
        355                 360                 365

Asp Pro His Ser Gly Ser Ile Val Thr Ser Gly Pro Thr Thr Ile Lys
    370                 375                 380

Asp Ser Asn Trp Leu Leu Gly Tyr Ser Ile Ser Arg Gln Pro His Phe
385                 390                 395                 400

Glu Ala Gln Lys Pro Asn Glu Leu Ile Val Trp Leu Tyr Gly Leu Phe
                405                 410                 415

Ser Asp Thr Lys Gly Asn Tyr Val Glu Lys Thr Met Pro Asp Cys Asn
            420                 425                 430

Gly Ile Glu Leu Cys Glu Glu Trp Leu Tyr His Met Gly Val Pro Glu
        435                 440                 445

Glu Arg Ile Pro Glu Met Ala Ser Ala Ala Thr Thr Ile Pro Ala His
    450                 455                 460

Met Pro Tyr Ile Thr Ser Tyr Phe Met Pro Arg Ala Leu Gly Asp Arg
465                 470                 475                 480

Pro Lys Val Val Pro Asp His Ser Lys Asn Leu Ala Phe Ile Gly Asn
                485                 490                 495

Phe Ala Glu Thr Pro Arg Asp Thr Val Phe Thr Thr Glu Tyr Ser Val
            500                 505                 510

Arg Thr Ala Met Glu Ala Val Tyr Thr Leu Leu Asn Ile Asp Arg Gly
        515                 520                 525

Val Pro Glu Val Phe Ala Ser Ala Phe Asp Val Arg Met Leu Met Asn
    530                 535                 540

Ala Met Tyr Tyr Leu Asn Asp Gln Lys Lys Leu Glu Asp Leu Asp Leu
545                 550                 555                 560

Pro Ile Ala Glu Lys Leu Ala Ile Lys Gly Met Leu Lys Lys Val Lys
                565                 570                 575

Gly Thr Tyr Ile Glu Glu Leu Leu Lys Lys Tyr Lys Leu Val
            580                 585                 590
```